(12) United States Patent
Greenberg et al.

(10) Patent No.: US 9,808,625 B2
(45) Date of Patent: Nov. 7, 2017

(54) SPATIAL FITTING BY PERCEPT LOCATION TRACKING

(71) Applicants: Robert J. Greenberg, Los Angeles, CA (US); Michael Barry, Baltimore, MD (US); Gislin Dagnelie, Baltimore, MD (US)

(72) Inventors: Robert J. Greenberg, Los Angeles, CA (US); Michael Barry, Baltimore, MD (US); Gislin Dagnelie, Baltimore, MD (US)

(73) Assignee: Second Sight Medical Products, Inc., Sylmar, CA (US)

( * ) Notice: Subject to any disclaimer, the term of this patent is extended or adjusted under 35 U.S.C. 154(b) by 4 days.

(21) Appl. No.: 15/144,616

(22) Filed: May 2, 2016

(65) Prior Publication Data

US 2016/0317812 A1 Nov. 3, 2016

Related U.S. Application Data

(60) Provisional application No. 62/156,119, filed on May 1, 2015.

(51) Int. Cl.
| | |
|---|---|
| *A61N 1/36* | (2006.01) |
| *A61N 1/05* | (2006.01) |
| *A61N 1/372* | (2006.01) |
| *G06F 19/00* | (2011.01) |

(52) U.S. Cl.
CPC ..... *A61N 1/36046* (2013.01); *G06F 19/3406* (2013.01); *A61N 1/0543* (2013.01); *A61N 1/37247* (2013.01)

(58) Field of Classification Search
None
See application file for complete search history.

(56) References Cited

U.S. PATENT DOCUMENTS

| | | |
|---|---|---|
| 5,109,844 A | 5/1992 | de Juan, Jr. et al. |
| 5,935,155 A | 8/1999 | Humayun et al. |
| 5,944,747 A | 8/1999 | Greenberg et al. |
| 6,400,989 B1 | 6/2002 | Eckmiller |
| 6,458,157 B1 | 10/2002 | Suaning |
| 6,718,209 B2 | 4/2004 | Williamson et al. |
| 6,974,533 B2 | 12/2005 | Zhou |
| 7,483,751 B2 | 1/2009 | Greenberg et al. |
| 7,493,169 B2 | 2/2009 | Greenberg et al. |
| 7,738,962 B2 | 6/2010 | Greenberg et al. |
| 7,818,064 B2 | 10/2010 | Greenberg et al. |
| 7,908,011 B2 | 3/2011 | McMahon et al. |
| 8,180,454 B2 | 5/2012 | Greenberg et al. |
| 8,195,301 B2 | 6/2012 | Roy et al. |
| 8,271,091 B2 | 9/2012 | McMahon et al. |
| 8,428,739 B2 * | 4/2013 | Ahuja ................ A61N 1/36046 607/53 |
| 2005/0201585 A1 | 9/2005 | Jannard et al. |

(Continued)

*Primary Examiner* — Brian T Gedeon
(74) *Attorney, Agent, or Firm* — Scott Dunbar

(57) ABSTRACT

The present invention is an improved spatial fitting and training system for a visual prosthesis. The system of the present invention maps projected locations of percepts, where a person perceives a percept from a visual prosthesis to the intended location of the percepts. The projected location may vary over time. This test results can be used to correct a visual prosthesis or spatially map the visual prosthesis.

11 Claims, 28 Drawing Sheets

(56) References Cited

U.S. PATENT DOCUMENTS

2005/0222624 A1 10/2005 Greenberg et al.
2006/0129207 A1 6/2006 Fried et al.
2010/0249878 A1* 9/2010 McMahon ........... A61N 1/0543
  607/54
2016/0303373 A1* 10/2016 Dorn .................... A61N 1/0543

* cited by examiner

SPATIAL FITTING BY PERCEPT LOCATION TRACKING

CROSS REFERENCE TO RELATED APPLICATIONS

The present application claims priority to U.S. Provisional Patent Application 62/156,119, filed May 1, 2015, for Spatial Fitting by Precept Location Tracking.

FIELD

The present disclosure relates to visual prostheses configured to provide neural stimulation for the creation of artificial vision, and more specifically, an improved method of fitting and training for a visual prosthesis.

BACKGROUND

Applicants have developed many methodologies for fitting an electrode array to a patient including: U.S. Pat. No. 8,271,091, for Visual prosthesis fitting; U.S. Pat. No. 8,195,301 Video configuration file editor for visual prosthesis fitting and related method; U.S. Pat. No. 8,190,267, for Fitting a neural prosthesis using impedance and electrode height; U.S. Pat. No. 8,180,454, for Fitting a neural prosthesis using impedance and electrode height; U.S. Pat. No. 7,908,011, for Visual prosthesis fitting; U.S. Pat. No. 7,818,064, for Fitting of brightness in a visual prosthesis; U.S. Pat. No. 7,738,962, for Fitting of brightness in a visual prosthesis; U.S. Pat. No. 7,493,169 for Automatic fitting for a visual prosthesis; U.S. Pat. No. 7,483,751, for Automatic fitting for a visual prosthesis. The preceding list includes both manual and automated fitting methods. Both have advantages and disadvantages. What is needed is a method that uses the best advantages of both manual and automatic fitting.

SUMMARY

The present invention is an improved spatial fitting and training system for a visual prosthesis. The system of the present invention maps projected locations of percepts (PLP), where a person perceives a percept from a visual prosthesis, to the intended location of the percepts. The projected location may vary over time. These test results can be used to correct a visual prosthesis or spatially map the visual prosthesis. While a patient can be initially fitted on a purely spatial basis, by correcting for the error of each PLP in a single session, understanding the change in PLP over time provides for a more accurate fit of the patient.

BRIEF DESCRIPTION OF THE FIGURES

FIGS. 20-1, 20-2, 20-3 and 20-4 show an exemplary embodiment of a video processing unit. FIG. 20-1 should be viewed at the left of FIG. 20-2. FIG. 20-3 should be viewed at the left of FIG. 20-4. FIGS. 20-1 and 20-2 should be viewed on top of FIGS. 20-3 and 20-4.

DETAILED DESCRIPTION

The present invention is an improved spatial fitting and training system for a visual prosthesis. The system of the present invention maps projected locations of percepts, where a person perceives a percept from a visual prosthesis, to the intended location of the percepts. The projected location may vary over time. This test results can be used to correct a visual prosthesis or spatially map the visual prosthesis.

Figure 1:
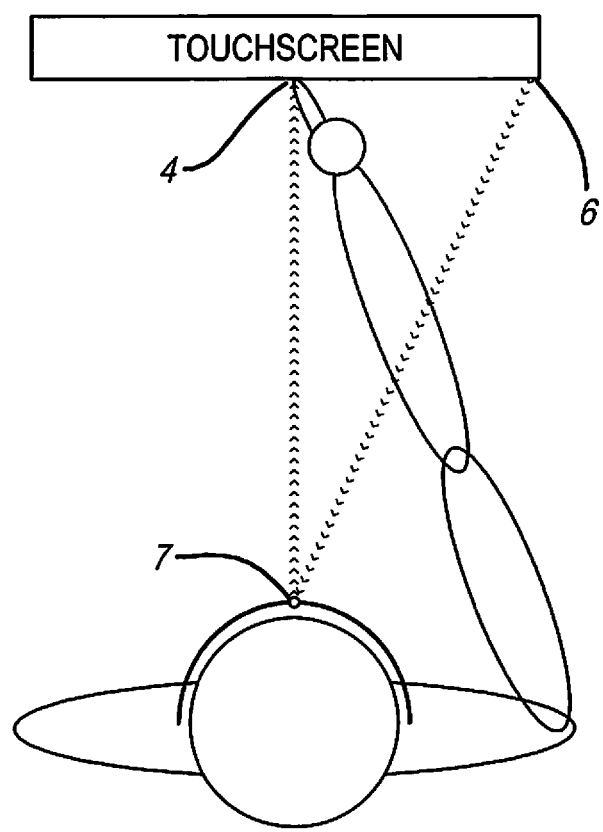
FIG. 1 is a diagram of a subject using the touch screen monitor to indicate the projected location of perception.

FIG. 1 shows a subject being fitting by the method of the present invention. The subject looks at a touch screen monitor 1 using the visual prosthesis via the visual prosthesis camera 7. A square is presented on the touch screen monitor 1 at the true location 6. The subject indicates the perceived location of percept (PLP) 4.

Subjects: 3 end-stage RP patients implanted with the Argus® II epiretinal prosthesis Experiment: Participants attempted to touch a white square target on a black background on a touchscreen monitor 1. Touchscreen dimensions: 37.5 cm×30 cm (~54°× 44° of visual field)

Touchscreen Resolution: 1024×768 pixels

Approximate camera-to-screen distance: 37 cm

Typical target size: 3 cm×3 cm (~4°×4° of visual field)

Typical number of trials (targets to touch) per trial run: 40

Trial runs per testing session (mean±SD): 6.0±7.7 (range=1-30)

Camera sampling position (CSP): position of the approximate 17.23°×10.21° area sampled for prosthesis processing out of the 66°×49° area captured by the prosthesis camera. CSPs were adjusted to reduce errors when necessary. PLPs were tracked over periods ranging 154-959 days.

Computer software recorded the location of each target and subject responses. Errors, in degrees of visual field, were calculated for each response. Errors were combined with CSPs to estimate PLPs for each trial. Trial PLPs were averaged within trial runs. 95% confidence intervals (CIs) were established for trial run PLPs based on t-distributions. To reduce bias introduced by CSPs, only trial run PLPs that contained their corresponding CSPs within their CIs, and that had within-subject smaller-than-average CIs, were considered for analysis.

Figure 5:
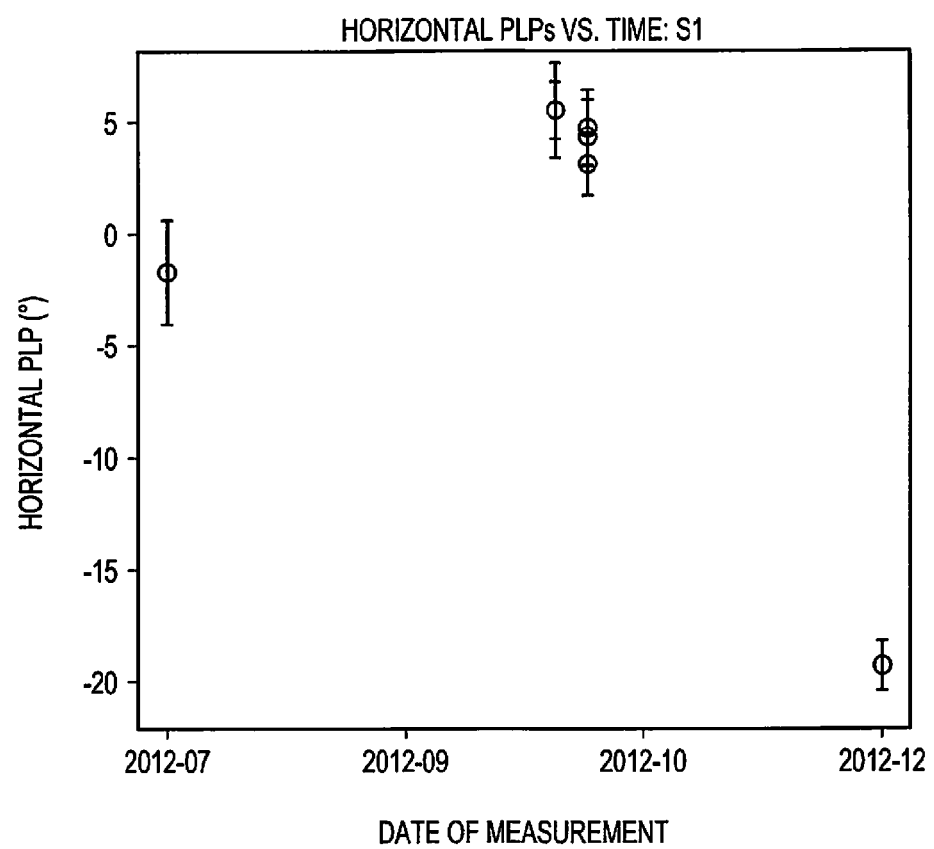
FIG. 5 shows the horizontal change in PLP over time for a first subject.
Figure 6:
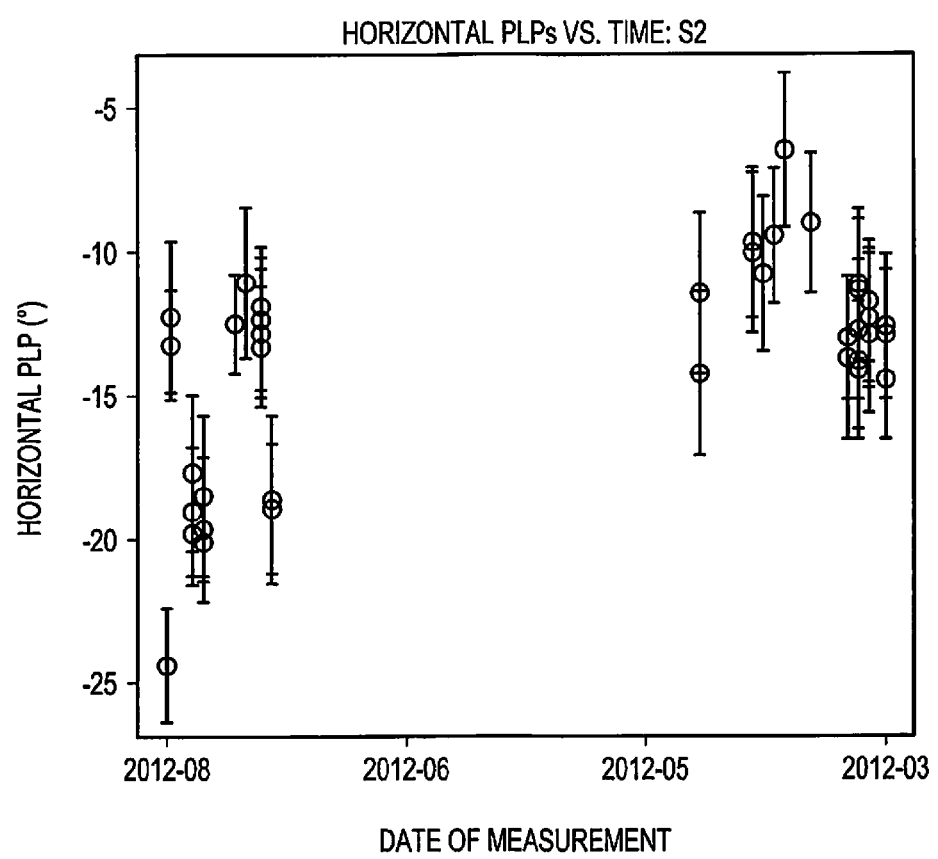
FIG. 6 shows the horizontal change in PLP over time for a second subject.
Figure 7:
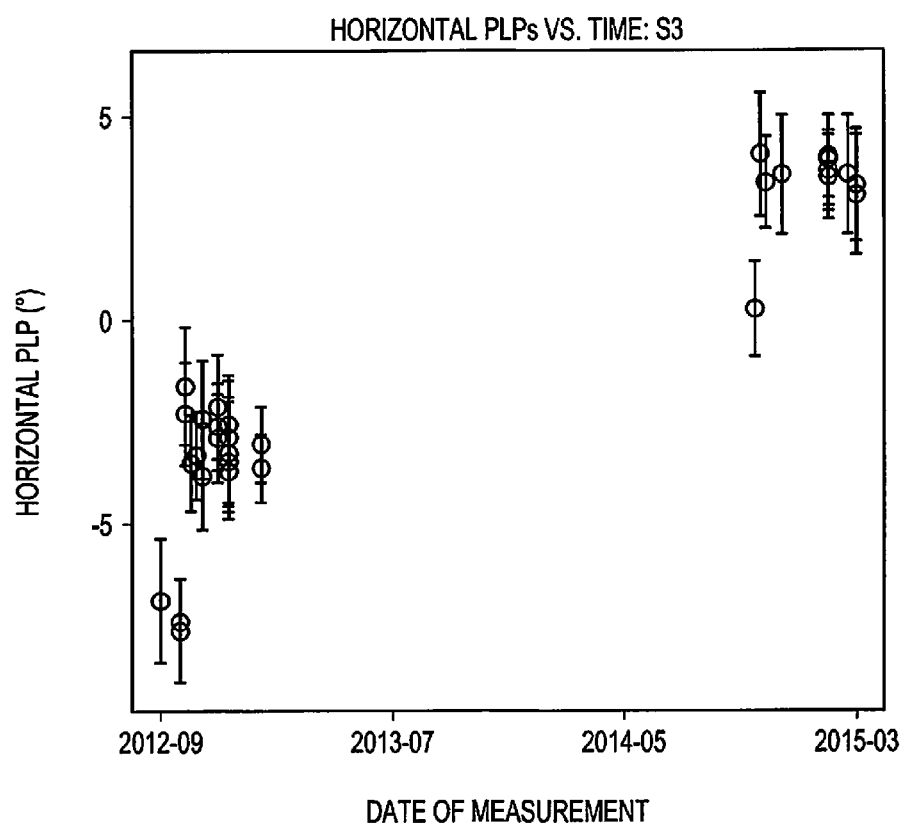
FIG. 7 shows the horizontal change in PLP over time for a third subject.
Figure 8:
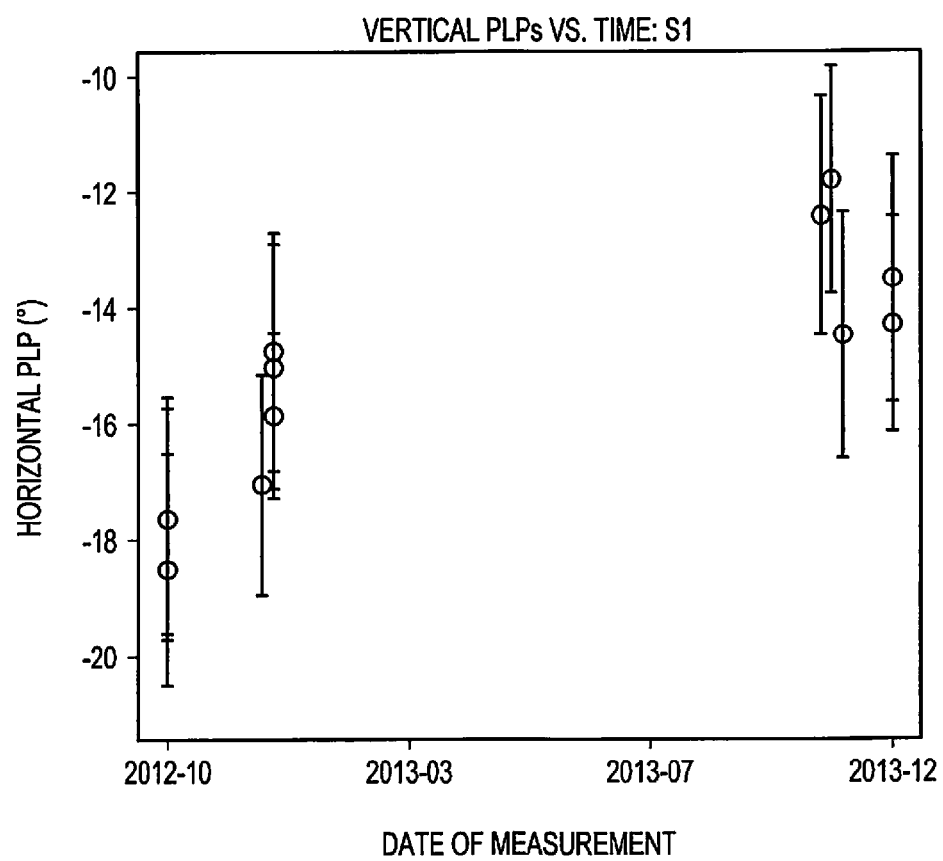
FIG. 8 shows the vertical change in PLP over time for a first subject.
Figure 9:
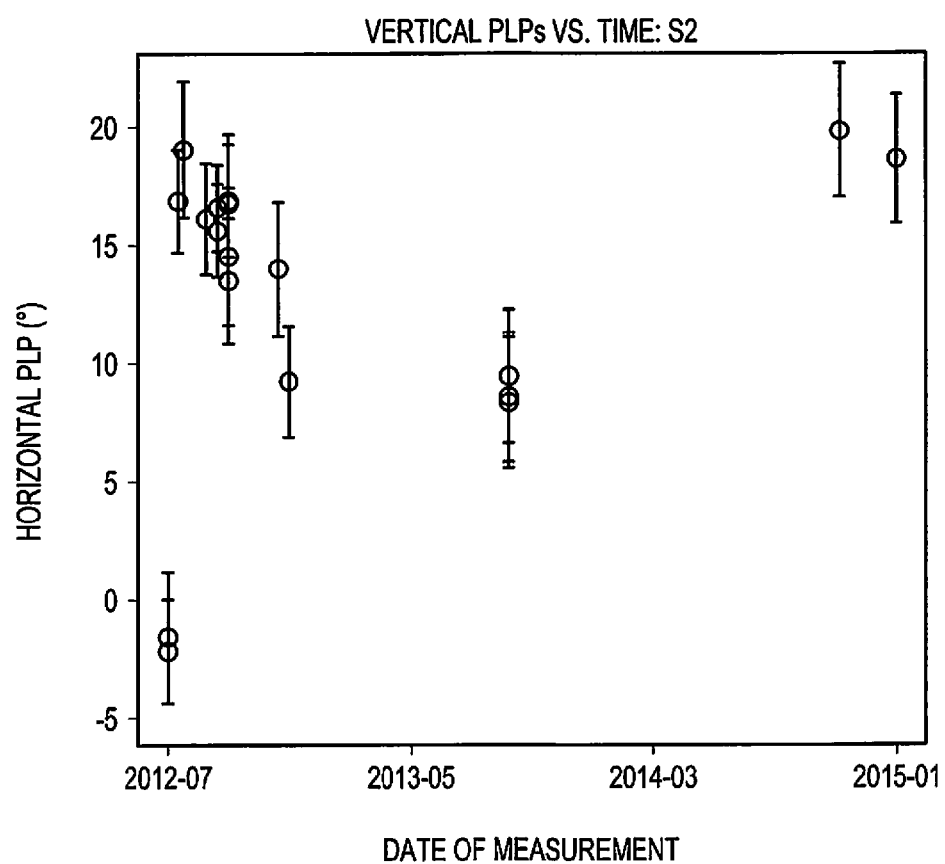
FIG. 9 shows the vertical change in PLP over time for a second subject.
Figure 10:
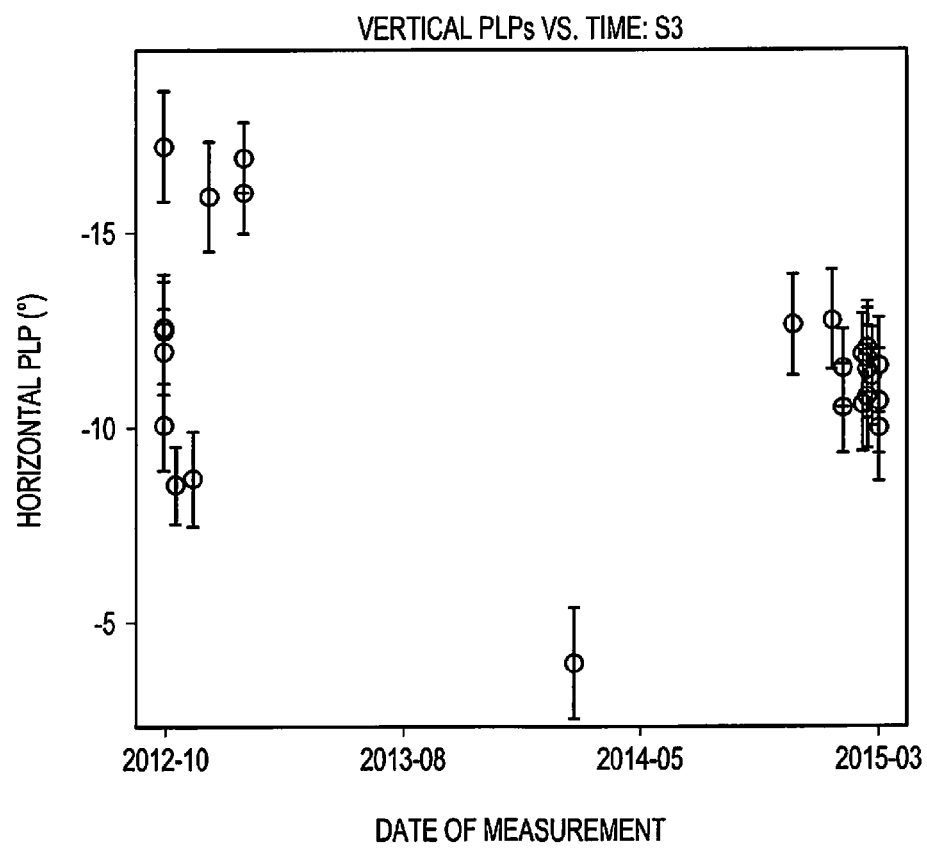
FIG. 10 shows the vertical change in PLP over time for a third subject.

Significance of horizontal (FIGS. 5-7) and vertical (FIGS. 8-10) differences in PLPs for individual subjects across trial runs was evaluated using a bootstrap variation of ANOVA. Only PLP measurements with non-intersecting confidence intervals were considered for calculating rates of significant change. Data compilation, statistical calculations, and plots were produced using R 3.1.3.

There was a significant effect of trial run (i.e., differences across time) on both horizontal and vertical components of PLPs for all three subjects ($p<10^{-4}$), not discernibly linked to any external parameters.

Within-subject ranges of fluctuation of PLP components:
Range: 6.7°-25°
Mean=16°
Standard deviation (SD)=6.8°.
Rates of significant change for PLP components:
Range: 1.3°/year–4.4°/hour
Mean=5.9°/day
Median=0.13°/day
SD=24°/day
No measured PLPs displayed long-term stability.

PLPs displayed a lack of long-term stability in all three subjects. Periods of short-term stability were broken by shifts as dramatic as up to 4.4°/hour. Rates of PLP change were highly variable, with a standard deviation of 24°/day. While we do not know precisely what causes these fluctuations, continuing research suggests eye movement patterns during stimulation might play a large role. As prosthesis subjects with constant corrective feedback display much slower rates of adaptation to inaccurate CSPs, and no adaptation without corrective feedback, regular recalibrations of prosthesis CPs are required to maintain subject hand-camera coordination. Feedback can come in multiple forms from a simply right or wrong indication to a detailed direction and distance correction.

Figure 2:
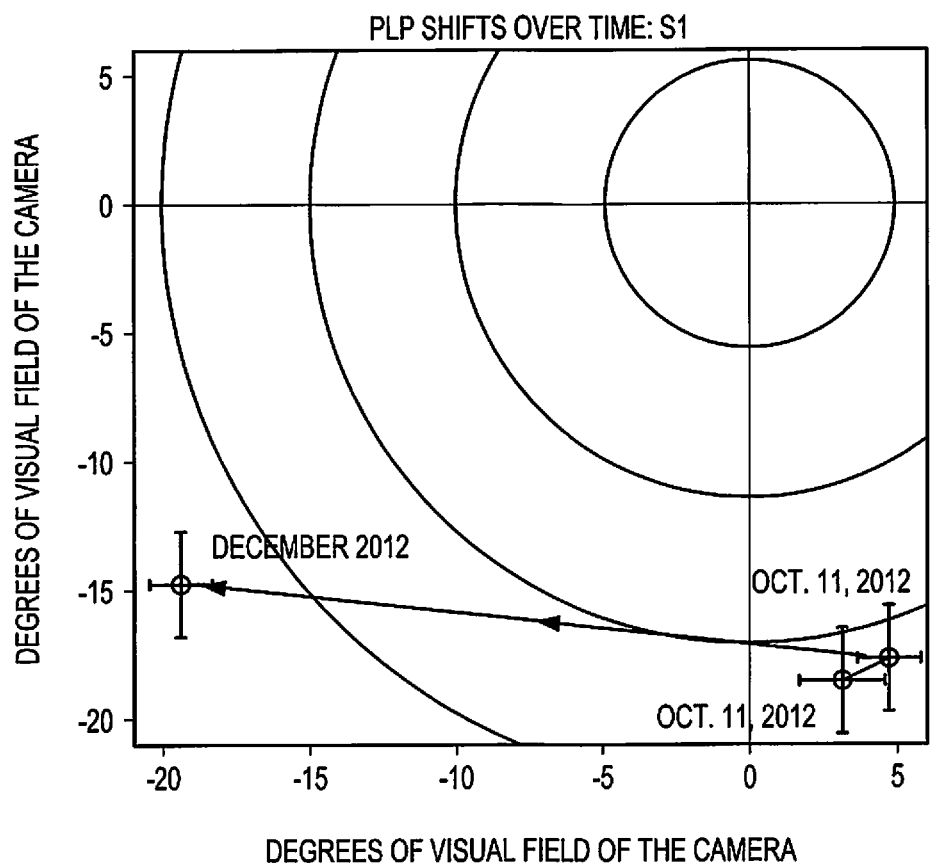
FIG. 2 shows the change in PLP over time for a first subject.
Figure 3:
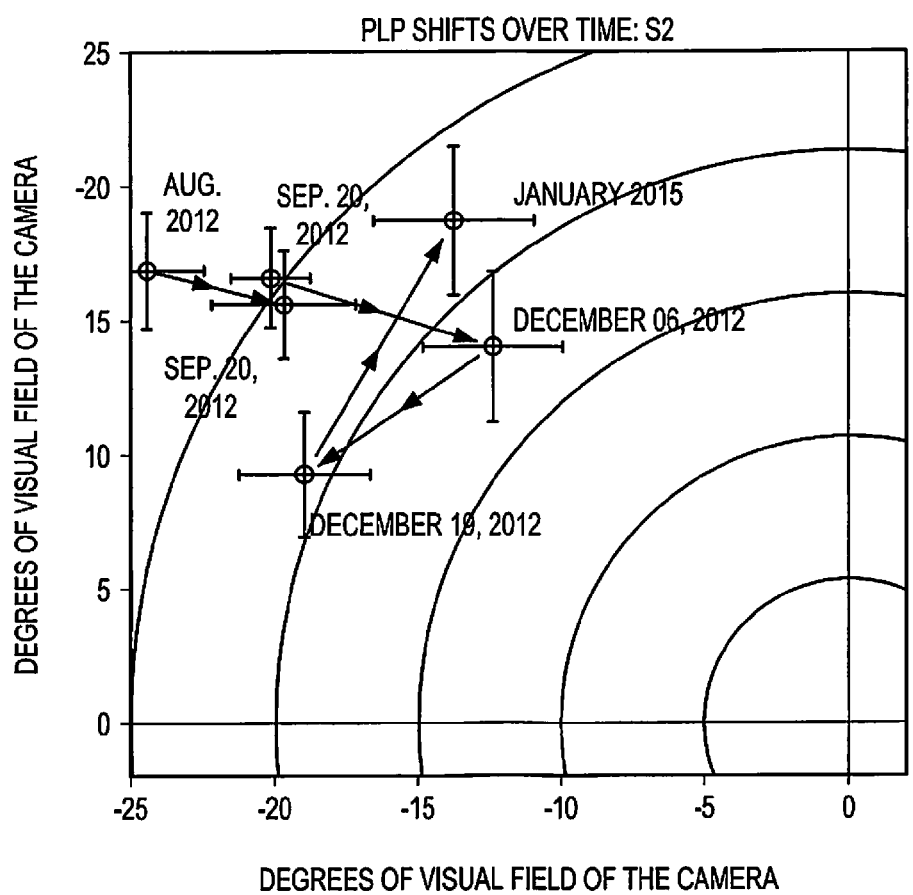
FIG. 3 shows the change in PLP over time for a second subject.
Figure 4:
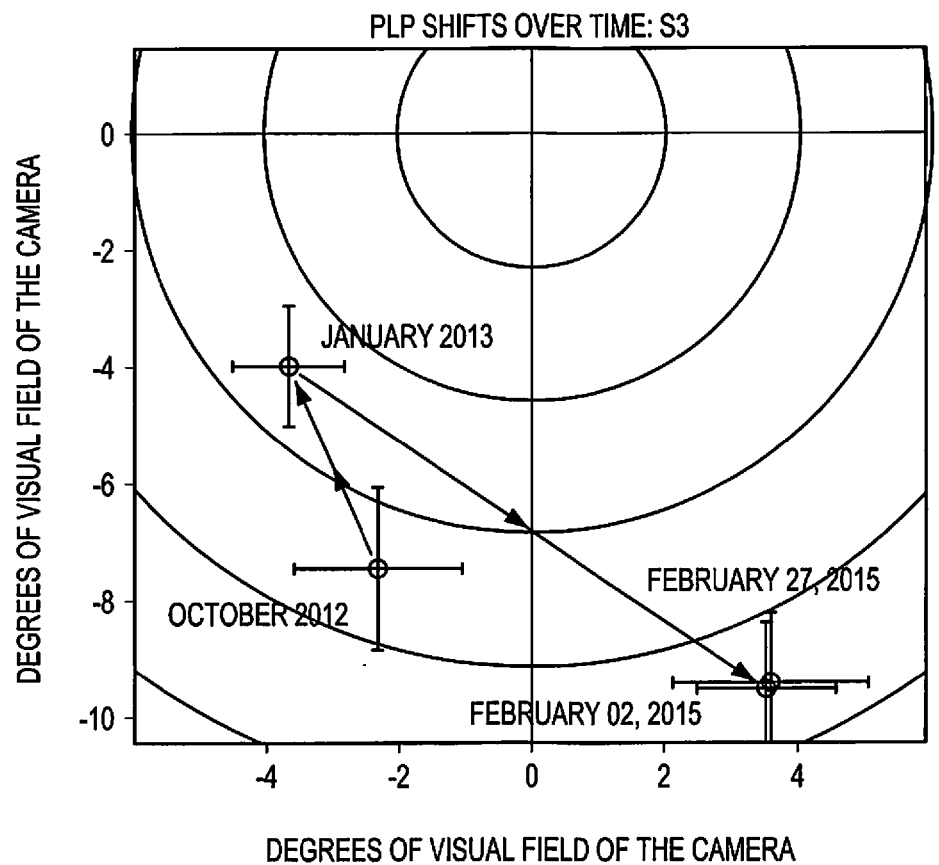
FIG. 4 shows the change in PLP over time for a third subject.

FIGS. 2-4 shows PLP estimates for three subjects, one subject each figure. The three subjects are denoted by descriptors S1, S2 and S3 to preserve patient privacy. PLP estimates from trial runs with S1 that simultaneously satisfied CI requirements in both horizontal and vertical directions. Error bars indicate 95% confidence intervals. Arrows indicate chronological order.

FIGS. 5-10 shows the PLP estimates separated for horizontal and vertical components. These plots separate horizontal and vertical PLP components for each subject, displayed against their dates of measurement. Error bars indicate 95% confidence intervals for each point, based on their corresponding trial runs.

Square or Circle Localization:

In the Square Localization test, a high-contrast white square (80×80 pixels, or 3 cm×3 cm) was presented in random locations on a 20" touch screen monitor 1 in front of the subject. When prompted, the subject scanned the monitor and located the square, touching the screen at the location of the square center. Subjects first completed a short practice run (10-trial), in which they selected the location of the square by touching the monitor where they wanted it to appear. Next, a 40-trial test was administered. No feedback was given to the subject during the test.

Figure 21:
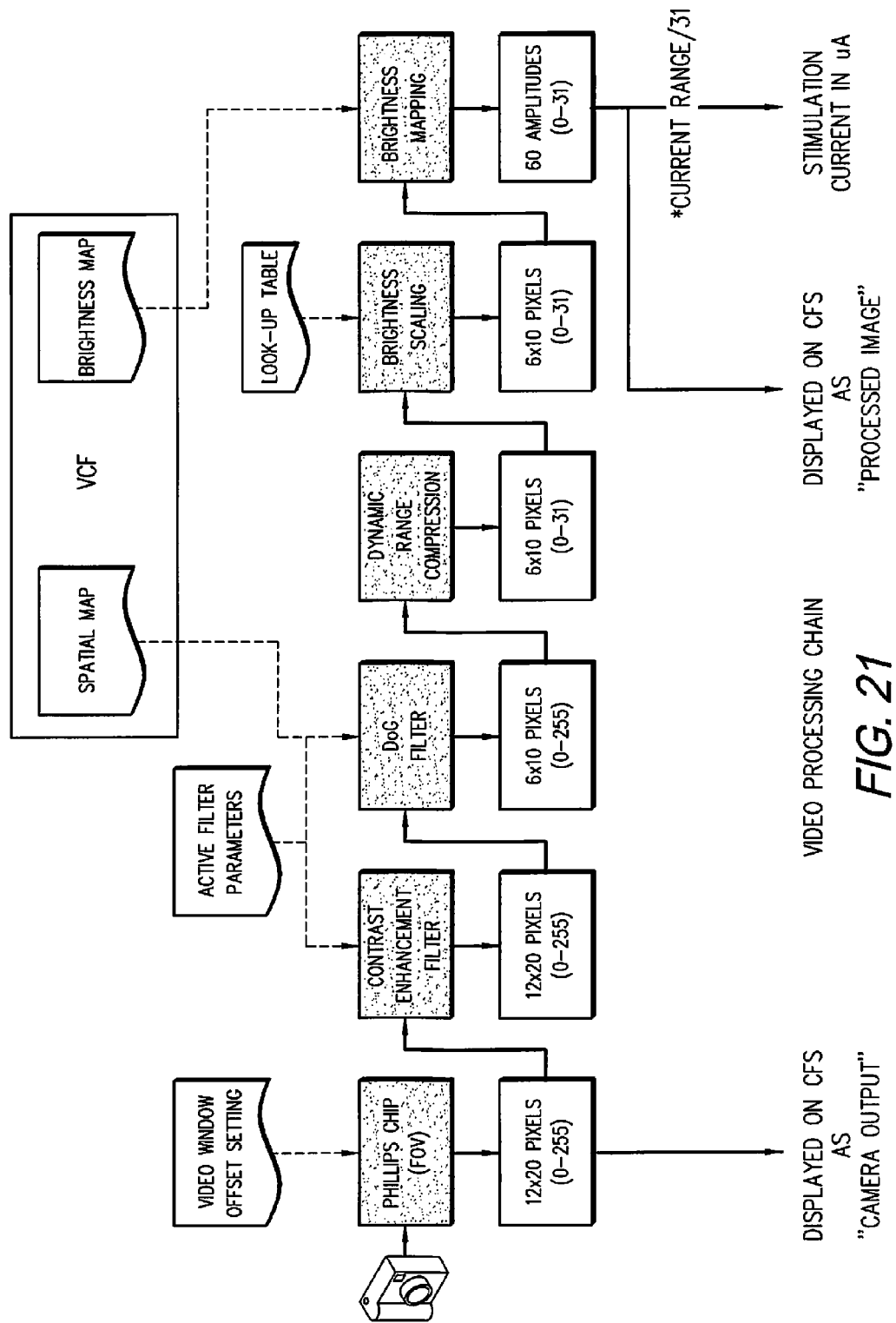
FIG. 21 is flow chart of the video processing chain in a visual prosthesis

Mean errors from the square localization assessment can be used to adjust the field of view the camera presents to the electrode array. This can be done by physically moving the camera angle with respect to the glasses or translating the camera position with respect to the glasses. This can also be done electronically by selecting the appropriate field of view from the camera signal to feed to the implant. Because the image captured by the camera and stored in memory is much larger than the field of view associated with the electrode array on the retina, electronic control can be accomplished by down-selecting an appropriate window of video data from the image. Refer to "Video Window offset Setting" with respect to FIG. 21.

Further, another shape such as circle or square with an intensity that is brightest at the center that gradual fades out may reduce edge effects and measurement error. The size of the shape could be set to the minimum the size that is detectable by the subject, further reducing the measurement error.

The x (horizontal) and y (vertical) location of the error centroid of the square localization assessment gives you the apparent location that the patient believes the percepts are appearing on average relative to the current camera alignment position. By correcting for this offset with camera position or field of view position, the patient's perceptions can be aligned with visual stimuli from the monitor. For example, if the error centroid was 1 degree to the right of the expected center location, the camera could be angled to the right by 1 degree (or the field of interest could be electronically moved to the right by 1 degree). This, of course, works in the vertical direction too.

It has been noted elsewhere that even sighted subjects have a large degree in of error in tasks of this type when they are not able to see their hand as they proceed to point to a target. There are other analyses besides mean and standard deviation that may be more advantageous. For instance, cluster analysis of the data would be helpful when the points fall into more than one region. A moment analysis (center of mass) approach where the pixels were weighted would also improve the precision of the point.

Further, it is also likely that the sources of error sum to locations with a probability density function that is not Gaussian, but rather could have several modes, and it is unlikely that the statistics of the random variables that characterize the measurement error are stationary within an electrode and ergodic over the ensemble of all of the electrodes. Thus non Gaussian distributions can be used to estimate the location of perception. This can include but is not limited to Binomial, Poison with parameter, Geometric with parameter, negative binomial with parameters, and Gamma with parameters. These distribution functions are known in the context of estimation, stochastics, and the characterization or random variables. In the case where the measurement errors are mixed, there will be a central location that is close to the true measurements, and overlapping data from probability distributions of the various error sources. In this case, minimum error classification can be used to select the most likely target to use when adjusting the camera. There are several types of appropriate minimum error classification methods that are known in the art.

A variant on the method discussed above is to make many measurements at one stimulation location and then use the estimated location to physically or electronically move the camera toward this location. This could be done with several other stimulation locations until the difference between the stimulation location and the presented square converge to within an acceptable limit.

In another embodiment, the sum of the errors over all electrodes could be used to set the convergence criterion.

Figure 15:
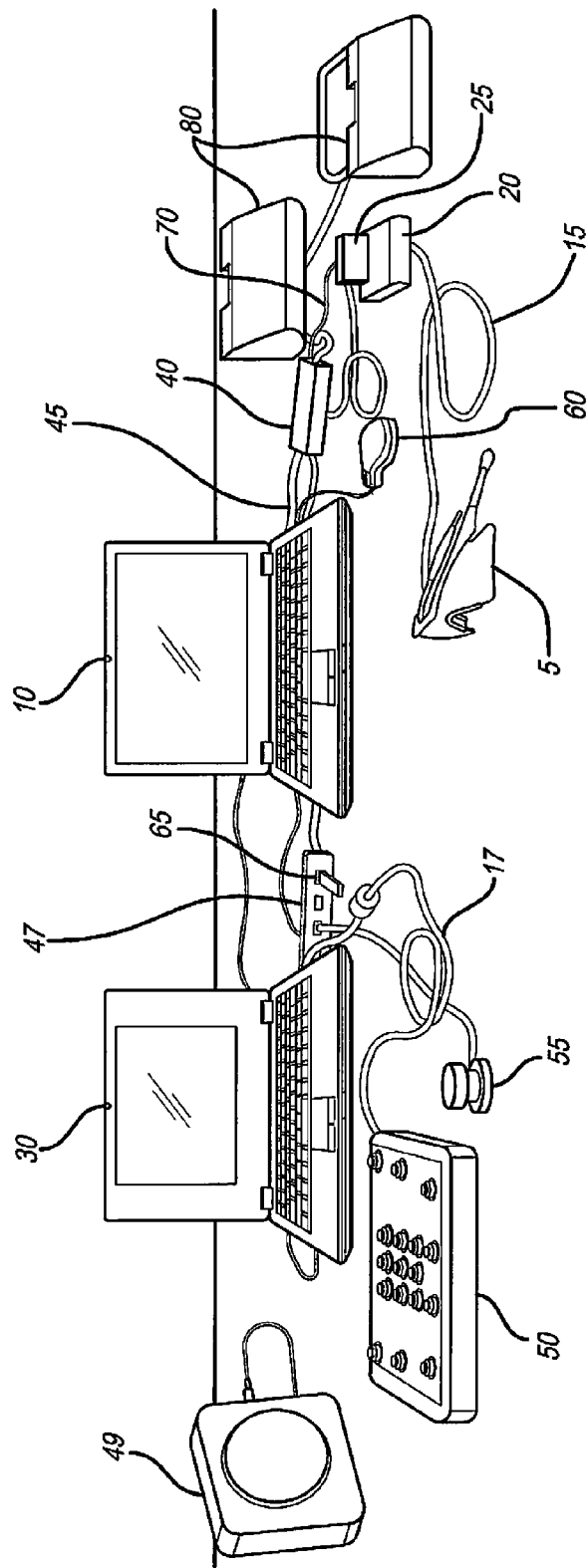
FIG. 15 shows components of a fitting system according to the present disclosure, the system also comprising the visor shown in FIGS. 13 and 14.

In another embodiment, using the preferred fitting system as shown in FIG. 15, an image may be adjusted manually by the following steps.

1. Be sure the touch screen monitor 1 is connected to the patient testing system (PTS) computer and set to be the primary monitor.

2. Adjust the height of touch screen monitor 1 so that the camera is pointed to the center of the touch screen.

3. Open the fitting software on the PTS laptop, change the directory to the folder containing "Camera Alignment" v1.00, type "runCameraAlignment" and hit Enter. Click on "Camera Position" button. A blank screen will appear on the touch screen.

4. Log in to the clinical fitting system (CFS) and select the "Psychophysics" tab. Log on to PTS and select the "Direct Stimulation" button. Make sure the subject's video processing unit (VPU) is on and connected to CFS and the subject is wearing the glasses.

5. In the PTS "Direct Stimulation" Screen, stimulate a small group of electrodes in the center of the array, and increase the stimulation amplitude and the number of stimulating electrodes until the subject clearly sees localized bright phosphenes.

6. Adjust the subject seating position and the touch screen monitor 1 in order to align the camera to the center of the touch screen and about 12" away from the screen. Instruct the subject to look straight ahead while keeping their head position as still as possible. Use a chin rest if necessary. Generate a phosphene using Direct Stimulation and ask the subject to point the location of the phosphene on the touch screen without moving their eyes or their head. If the position of the phosphene is not on the touch screen, move the touch screen or adjust the height of the subject's chair so that the response is on the monitor. Verify that a gray symbol appears on the touch screen at the location indicated by the subject.

7. Repeat the stimulation and gather a response 8 times. The touch screen will display all the outputs from the subject. Click the "Undo last trial" button to remove the last responses from the subject if necessary. Click the "Back" button to go back to the main screen and click the "Exit" button to exit the program. If the touch screen monitor 1 or the subject seating is adjusted during this step, repeat the step to collect 8 responses.

8. The program will calculate the average position of the responses and present an alignment target (a white circle) centered at this position on the touch screen.

9. Log out of PTS. Select the "CamPos" tab in CFS. Instruct the subject to look straight ahead and to carefully maintain the same head and body position as during the data collection phase. The alignment target should appear in "CamPos" screen. If not, use the right arrow key on the PTS to increase the size of the alignment target until it appears on the "CamPos" screen. Adjust the top, bottom, left, and right arrows on the CFS screen until the alignment target on the touch screen appears at the center of the "CamPos" screen. Reduce the alignment target size if necessary by pressing the left arrow key on the PTS. Click the "save" button on the CFS "CamPos" screen when the alignment target is at the center of the screen. This will select and store the section of the camera image that is aligned with the implant's visual field position on the subject's VPU. Record the saved camera position in the CRF.

10. Run the Square Localization test again to compare with the baseline data.

The ellipse from the square localization assessment is also useful in setting up the field of view of the electrode array. The area of the ellipse might be used to adjust the zoom of the camera—ie. one might 'zoom out' for a large ellipse or 'zoom in' for a small ellipse. Also, the orientation of the ellipse could be used to adjust the angle or tilt of the camera or field of view. Finally, after adjusting for angle, if the ellipse is not a circle, the ellipse could be used to adjust the horizontal and vertical zoom independently. So, if the ellipse was longer horizontally, a larger horizontal field of view compared to the vertical field of view could be selected.

One additional advantage of the approach is for setting the camera position/field of view is that the entire process can be automated. Thus, a patient can sit in front of a screen that presents individual square stimuli. The patient then touches the touch screen where he/she believes they saw the spot of light. This is repeated for an entire set of locations. The data is then analyzed in real-time (automatically) as described above and automatically downloaded to the VPU to adjust the camera field of view in real-time. In fact, this can be done during the course of the experiment such that data is taken, the field of view adjusted and more data is taken to confirm that the alignment was completed successfully.

Similarly, the direction of motion software can be used to adjust and confirm camera/field of view angle with respect to the horizon. The camera can be rotated (physically or electronically) in real-time until the number of correct responses at zero degrees is maximized. Alternately, the area under the response curve can be integrated and the mean value calculated such that the angle which minimizes the mean value is chosen.

Two spatial vision tests have been developed to supplement Grating Visual Acuity, our primary clinical trial endpoint. These assessment tools, the Square Localization and Direction of Motion tests in the Argus Training Program, were developed to provide an objective measure of spatial vision in subjects who do not reach the lowest levels of the Grating Acuity scale (2.9 logMAR), but who still receive useful spatial information by using the Argus II system. The Square Localization and Direction of Motion tests, device ON and device OFF, were administered to all US Argus II subjects who had been implanted at least 6 months ago (see below for the sole exception).

During the period in which subjects used misaligned CAPs and testing included auditory feedback, two of three subjects showed some significant improvement in accuracy. Improvement was very slow, averaging 0.02°/day. Subject S1 showed a total average decrease in error centroid distance of 6° during this period. S2's decrease in centroid distance was not statistically significant, and only fell on average by 0.4°. S3 showed a significant decrease of 4°.

When auditory feedback was removed, localization errors significantly increased over time for S1 and S2. S3 displayed a nonsignificant reduction in errors over time, but the expected error centroid distance for the last time point of the linear model of the feedback-ON period and its confidence interval were lower than any observed distance in the feedback-OFF period. Final error magnitudes were thus higher at the end of this observation period than before auditory feedback was removed. Comparing linear model expectations at the end of the feedback-OFF period with those at the end of the feedback-ON period, centroid distance significantly increased by 7° for S1, 4° for S2, and 4° for S3.

Over the entire time that subjects used misaligned CAPs, none reported any problematic percepts. None of the subjects had difficulty using their systems or noticed any discrepancies between their visual percepts and their other senses. When asked to simultaneously view and hold an illuminated rod, subjects could detect changes in where they localized the light when different CAPs were set, but did not readily perceive any sensory discordance.

Figure 11:
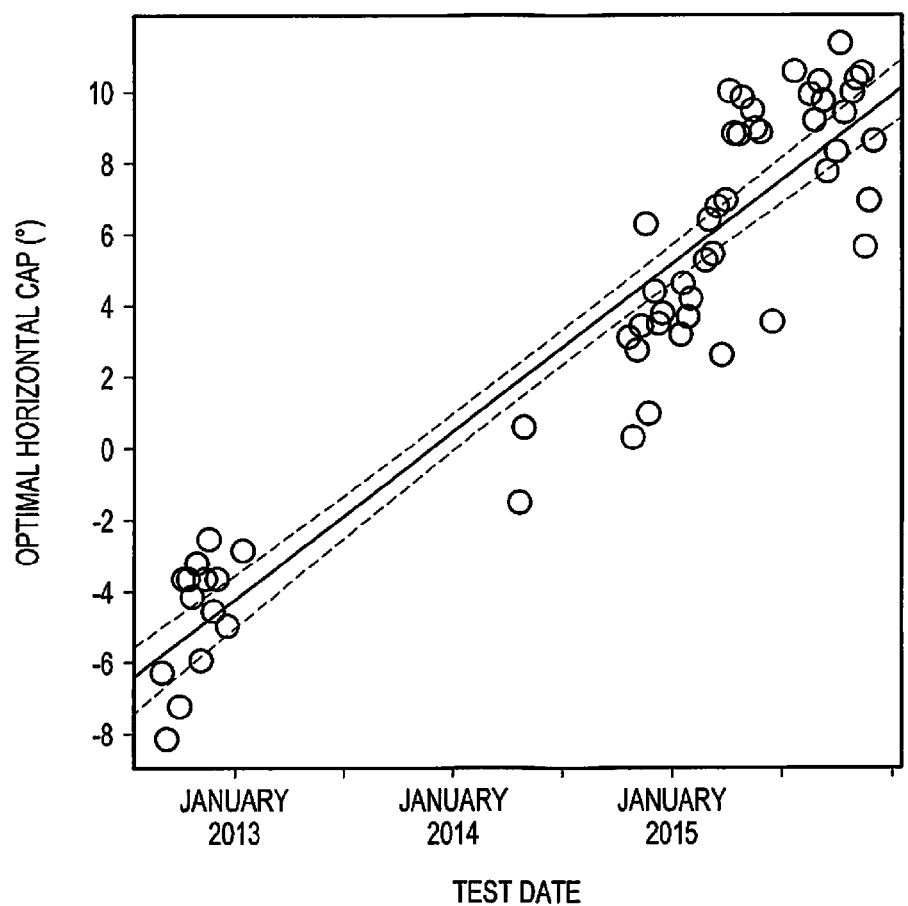
FIG. 11 shows the reduction in error centroid distances over time.

While little adaptation to misaligned CAPs was observed, CAPs required for proper alignment did fluctuate in all subjects. CAPs that provided optimal localization accuracy to subjects for a time eventually required adjustment to restore accuracy. MANOVA tests found significant effects of time: $p<10^{-4}$ for all subjects. Maximum differences between optimal CAPs for each subject were: 23° for S1, 29° for S2, and 21° for S3. Optimal CAP rates of change pooled across subjects had a median of 0.28°/day, mean of 0.39°/day, standard deviation of 0.36°/day, and maximum rate of 1.8°/day. Certain patterns did appear in how CAP estimates moved over time: optimal CAPs for S2 tended to move up and to the right over the observed period, and S3's optimal CAPs moved very consistently to the right. Changes over time in S3's optimal horizontal CAPs are highlighted in FIG. 11. Other observed shifts were less predictable: S1 displayed a weak rightward trend no apparent vertical trend over time, and S3' vertical shifts only weakly trended downward.

Figures 12A, 12B, 12C:
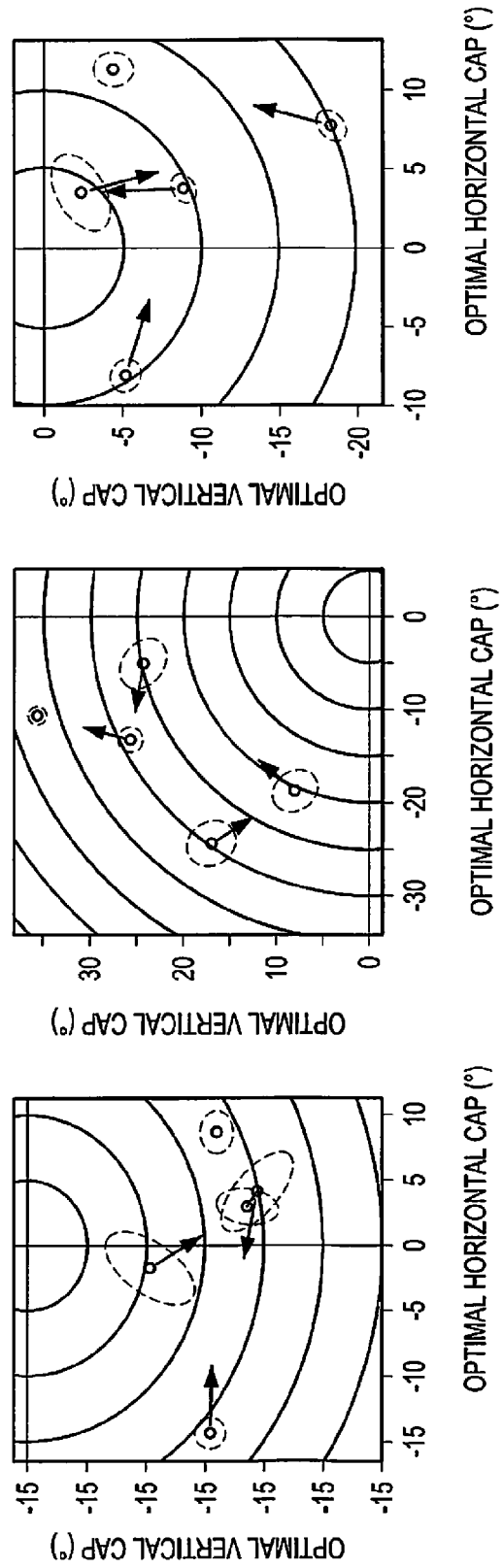
FIG. 12A shows relative increases in localization errors when no feedback was provided for S1.
FIG. 12B shows relative increases in localization errors when no feedback was provided for S2.
FIG. 12C shows relative increases in localization errors when no feedback was provided for S3.

FIGS. 12A-12C show examples of subjects' estimated optimal CAPs that differed significantly over time. For each subject, up to 4 points indicate the horizontal and vertical limits of optimal CAP positions and 1 point indicates the closest observation to the overall average optimal CAP. Arrows on the 4 first points in chronological order have arrows that point to the displayed CAP estimate that is next in chronological order.

Visual prostheses with extraocular cameras require calibration to optimize user hand-camera coordination. Camera input and/or processing can be changed to improve or degrade pointing accuracy. When users' cameras were not properly configured, those in this study did not seem to fully appreciate the nature of the misalignments. Passive adaptation to misalignments, i.e. without specific instruction and coaching from someone such as a rehabilitation specialist, was possible, but only with very slow progress. Rates of adaptation seen here were about 4000 times slower than those for normally sighted subjects wearing prism glasses (Gibson, 1933). S2 did not show significant localization improvement while auditory feedback was enabled, in contrast to our two other subjects. S2 was less diligent in providing precise responses, which added more variability to localization data and may have accompanied paying less attention to auditory feedback. Both of these factors would make observing significant improvement less likely.

Without consistent auditory feedback on in-lab localization errors, pointing accuracy deteriorated for all of our subjects. Error magnitudes increased immediately after auditory feedback was removed for S1 and S3, and only gradually increased for S2. This difference could once again be explained by S2's less diligent approach: if S2 was paying relatively little attention to the feedback, one would not expect removing the feedback to have as great an effect on responses. The gradual yet distinct increase in S2's errors after feedback was removed, however, does suggest that the feedback worked to maintain the subject's accuracy, if not improve it. For S1 and S3, the immediate increases in error magnitude may reflect the feedback acting as a reminder for the subjects to attend more carefully to how they respond, alongside providing information necessary for adaptation.

One might expect daily activities to provide corrective feedback on camera misalignments, such as reaching for a white mug against a dark background and missing. Unfortunately, subjects in this study did not appear to encounter or register enough of that information to improve or maintain pointing accuracy. It is possible that rehabilitation specialists familiar with visual prostheses and camera misalignments could teach users to detect and adjust to misalignments in their home environments. Further, a variation of the localization test used in this study that provides more precise feedback and allows users to make multiple attempts for one target could promote faster adaptation. The results of this study are restricted to contexts that do not involve specific coaching or devices designed to actively train users on correcting localization errors.

Lacking the ability to readily and independently adapt to misaligned percepts, the flexible nature of how prosthetic visual input is integrated into the perception of egocentric space is a point of concern. If users consistently required the same CAP to maintain hand-camera coordination, prosthesis systems would only need to be properly configured once. If a CAP initially set to maximize pointing accuracy becomes less suitable over time, however, and users cannot independently adapt to emergent misalignments, more frequent system calibrations will be required.

Some of the variation seen here may stem purely from the alignment and measurement processes used in this study; however, the consistent trends displayed over time by S2 and S3 suggest that at least part of this variability was intrinsic to the subjects. If variability originating from the subject could be explained by something as simple as how the eye rests in the orbit, prosthesis-integrated eye tracking mechanisms may be able to adjust CAPs automatically. If more complicated problems are involved, such as changing alignments of visual and proprioceptive percepts, more involved rehabilitation training or device programming may be needed to maintain optimal hand-camera coordination.

Figure 13:
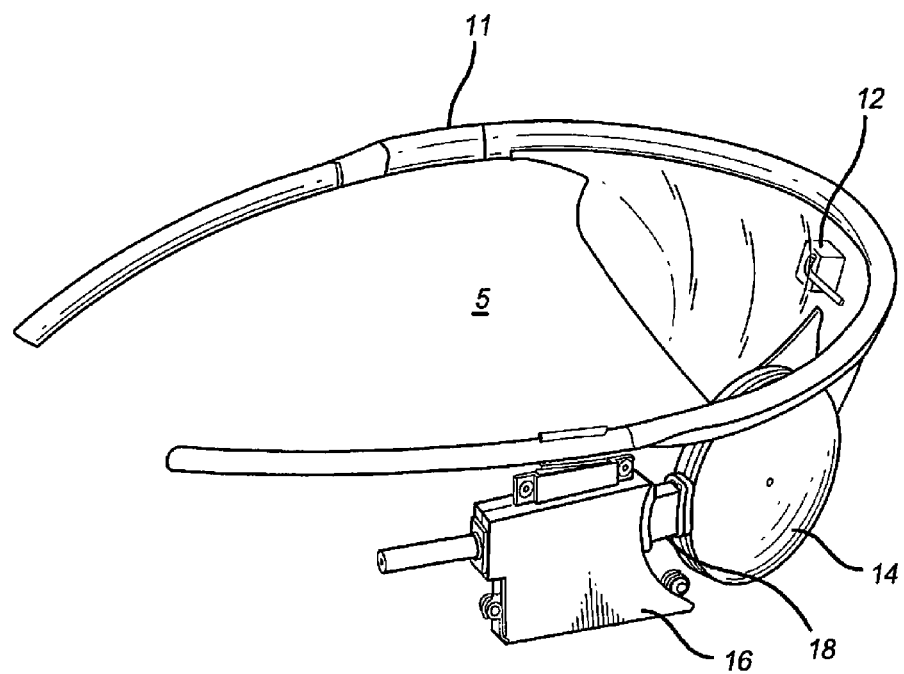
FIGS. 13 and 14 show a video capture/transmission apparatus or visor adapted to be used in combination with the retinal stimulation of FIGS. 22 and 23.
Figure 14:
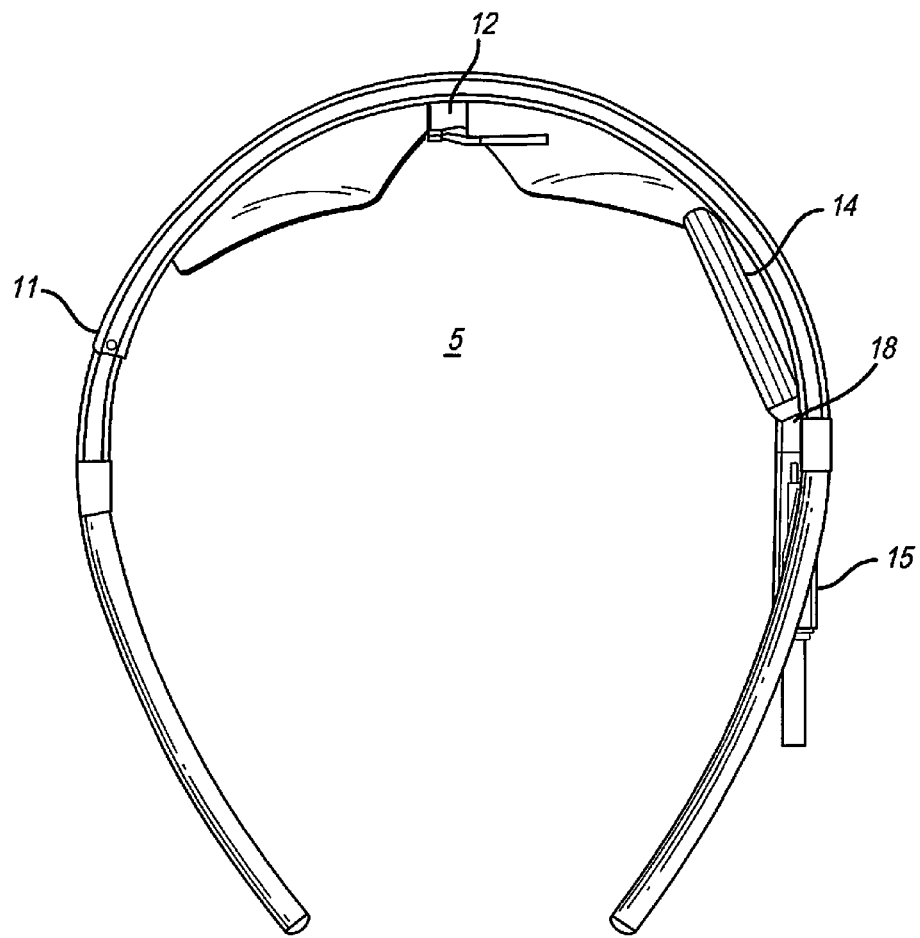

Referring to FIGS. 13 and 14, the glasses 5 may comprise, for example, a frame 11 holding a camera 12, an external coil 14 and a mounting system 16 for the external coil 14. The mounting system 16 may also enclose the RF circuitry. In this configuration, the video camera 12 captures live video. The video signal is sent to an external Video Processing Unit (VPU) 20 (shown in FIGS. 15 through 18 and discussed below), which processes the video signal and subsequently transforms the processed video signal into electrical stimulation patterns or data. The electrical stimulation data are then sent to the external coil 14 that sends both data and power via radio-frequency (RF) telemetry to the coil 116 of the retinal stimulation system 1, shown in FIGS. 22 through 25. The coil 116 receives the RF commands which control the application specific integrated circuit (ASIC) which in turn delivers stimulation to the retina of the subject via a thin film electrode array (TFEA). In one aspect of an embodiment, light amplitude is recorded by the camera 12. The VPU 20 may use a logarithmic encoding scheme to convert the incoming light amplitudes into the electrical stimulation patterns or data. These electrical stimulation patterns or data may then be passed on to the Retinal Stimulation System 1, which results in the retinal cells being stimulated via the electrodes in the electrode array 2010 (shown in FIG. 22). In one exemplary embodiment, the electrical stimulation patterns or data being transmitted by the external coil 14 is binary data. The external coil 14 may contain a receiver and transmitter antennae and a radio-frequency (RF) electronics card for communicating with the internal coil 116.

Figure 22:
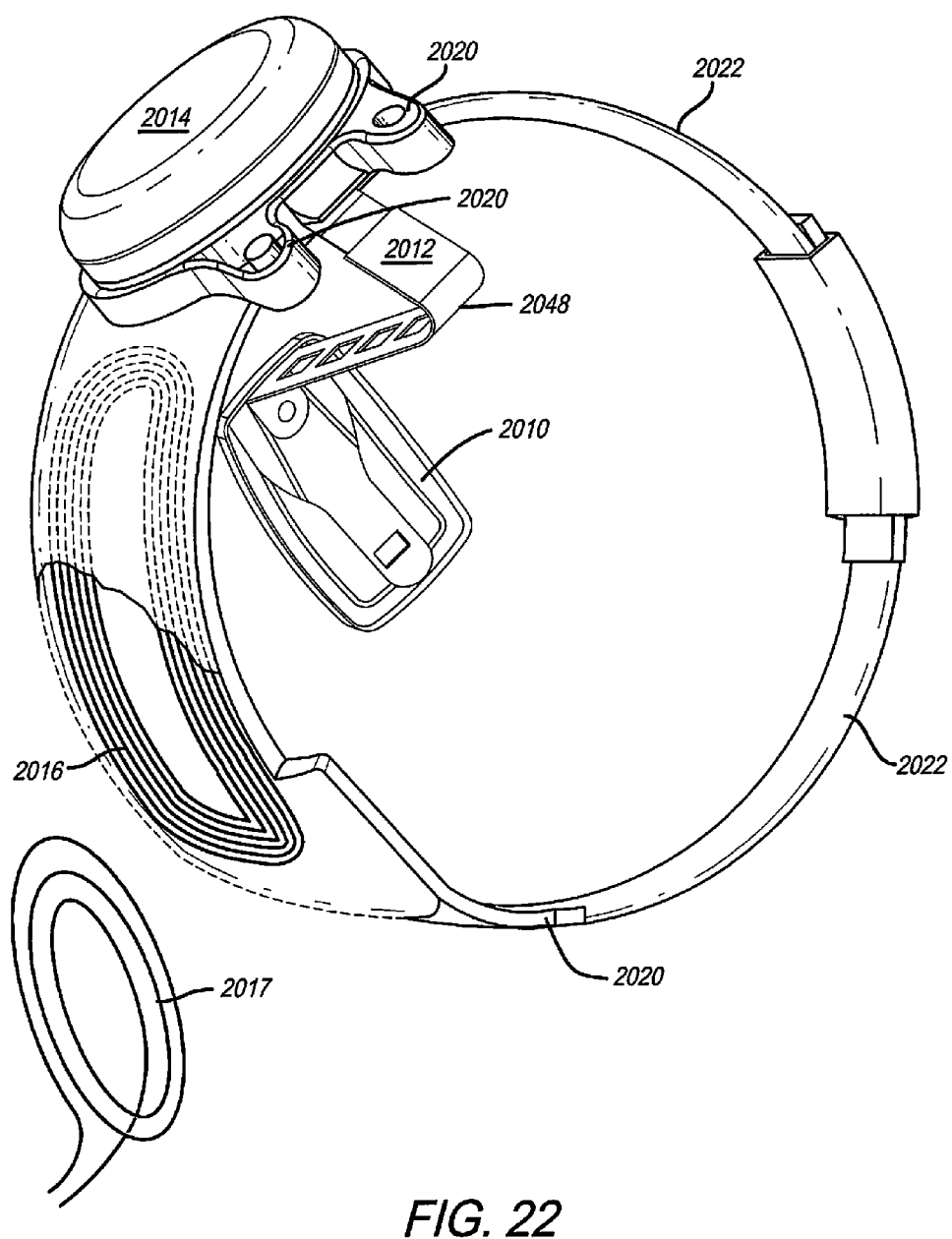
FIG. 22 is a perspective view of the implanted portion of the preferred visual prosthesis.

Referring to FIG. 15, a Fitting System (FS) may be used to configure and optimize the visual prosthesis apparatus shown in FIG. 22. The Fitting System is fully described in the related application U.S. application Ser. No. 11/796,425, filed on Apr. 27, 2007, which is incorporated herein by reference in its entirety.

The Fitting System may comprise custom software with a graphical user interface running on a dedicated laptop computer 10. Within the Fitting System are modules for performing diagnostic checks of the implant, loading and executing video configuration files, viewing electrode voltage waveforms, and aiding in conducting psychophysical experiments. A video module can be used to download a video configuration file to the Video Processing Unit (VPU) 20 discussed above and store it in non-volatile memory to control various aspects of video configuration, e.g. the spatial relationship between the video input and the electrodes. The software can also load a previously used video configuration file from the VPU 20 for adjustment.

The Fitting System can be connected to the Psychophysical Test System (PTS), located for example on a dedicated laptop 30, in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB® (MathWorks)™ software and other tools to allow the clinicians to develop customized psychophysics experiment scripts.

Using the psychophysics module, important perceptual parameters such as perceptual threshold, maximum comfort level, and spatial location of percepts may be reliably measured. Based on these perceptual parameters, the fitting software enables custom configuration of the transformation between video image and spatio-temporal electrode stimulation parameters in an effort to optimize the effectiveness of the visual prosthesis for each subject.

The Fitting System laptop 10 of FIG. 15 may be connected to the VPU 20 using an optically isolated serial connection adapter 40. Because it is optically isolated, the serial connection adapter 40 assures that no electric leakage current can flow from the Fitting System laptop 10 in the even of a fault condition.

As shown in FIG. 15, the following components may be used with the Fitting System according to the present disclosure. The Video Processing Unit (VPU) 20 for the subject being tested, a Charged Battery 25 for VPU 20, the Glasses 5, a Fitting System (FS) Laptop 10, a Psychophysical Test System (PTS) Laptop 30, a PTS CD (not shown), a Communication Adapter (CA) 40, a USB Drive (Security) (not shown), a USB Drive (Transfer) 47, a USB Drive (Video Settings) (not shown), a Patient Input Device (RF Tablet) 50, a further Patient Input Device (Jog Dial) 55, Glasses Cable 15, CA-VPU Cable 70, FS-CA Cable 45, FS-PTS Cable 46, Four (4) Port USB Hub 47, Mouse 60, Test Array system 80, Archival USB Drive 49, an Isolation Transformer (not shown), adapter cables (not shown), and an External Monitor (not shown).

With continued reference to FIG. 15, the external components of the Fitting System may be configured as follows. The battery 25 is connected with the VPU 20. The PTS Laptop 30 is connected to FS Laptop 10 using the FS-PTS Cable 46. The PTS Laptop 30 and FS Laptop 10 are plugged into the Isolation Transformer (not shown) using the Adapter Cables (not shown). The Isolation Transformer is plugged into the wall outlet. The four (4) Port USB Hub 47 is connected to the FS laptop 10 at the USB port. The mouse 60 and the two Patient Input Devices 50 and 55 are connected to four (4) Port USB Hubs 47. The FS laptop 10 is connected to the Communication Adapter (CA) 40 using the FS-CA Cable 45. The CA 40 is connected to the VPU 20 using the CA-VPU Cable 70. The Glasses 5 are connected to the VPU 20 using the Glasses Cable 15.

In one exemplary embodiment, the Fitting System shown in FIG. 15 may be used to configure system stimulation parameters and video processing strategies for each subject outfitted with the visual prosthesis apparatus. The fitting application, operating system, laptops 10 and 30, isolation unit and VPU 20 may be tested and configuration controlled as a system. The software provides modules for electrode control, allowing an interactive construction of test stimuli with control over amplitude, pulse width, and frequency of the stimulation waveform of each electrode in the Retinal stimulation system 1. These parameters are checked to ensure that maximum charge per phase limits, charge balance, and power limitations are met before the test stimuli are presented to the subject. Additionally, these parameters may be checked a second time by the VPU 20's firmware. The Fitting System shown in FIG. 15 may also provide a psychophysics module for administering a series of previously determined test stimuli to record subject's responses. These responses may be indicated by a keypad 50 and or verbally. The psychophysics module may also be used to reliably measure perceptual parameters such as perceptual threshold, maximum comfort level, and spatial location of percepts. These perceptual parameters may be used to custom configure the transformation between the video image and spatio-tempral electrode stimulation parameters thereby optimizing the effectiveness of the visual prosthesis for each subject. The Fitting System is fully described in the related application U.S. application Ser. No. 11/796,425, filed on Apr. 27, 2007, which is incorporated herein by reference in its entirety.

Figure 16:
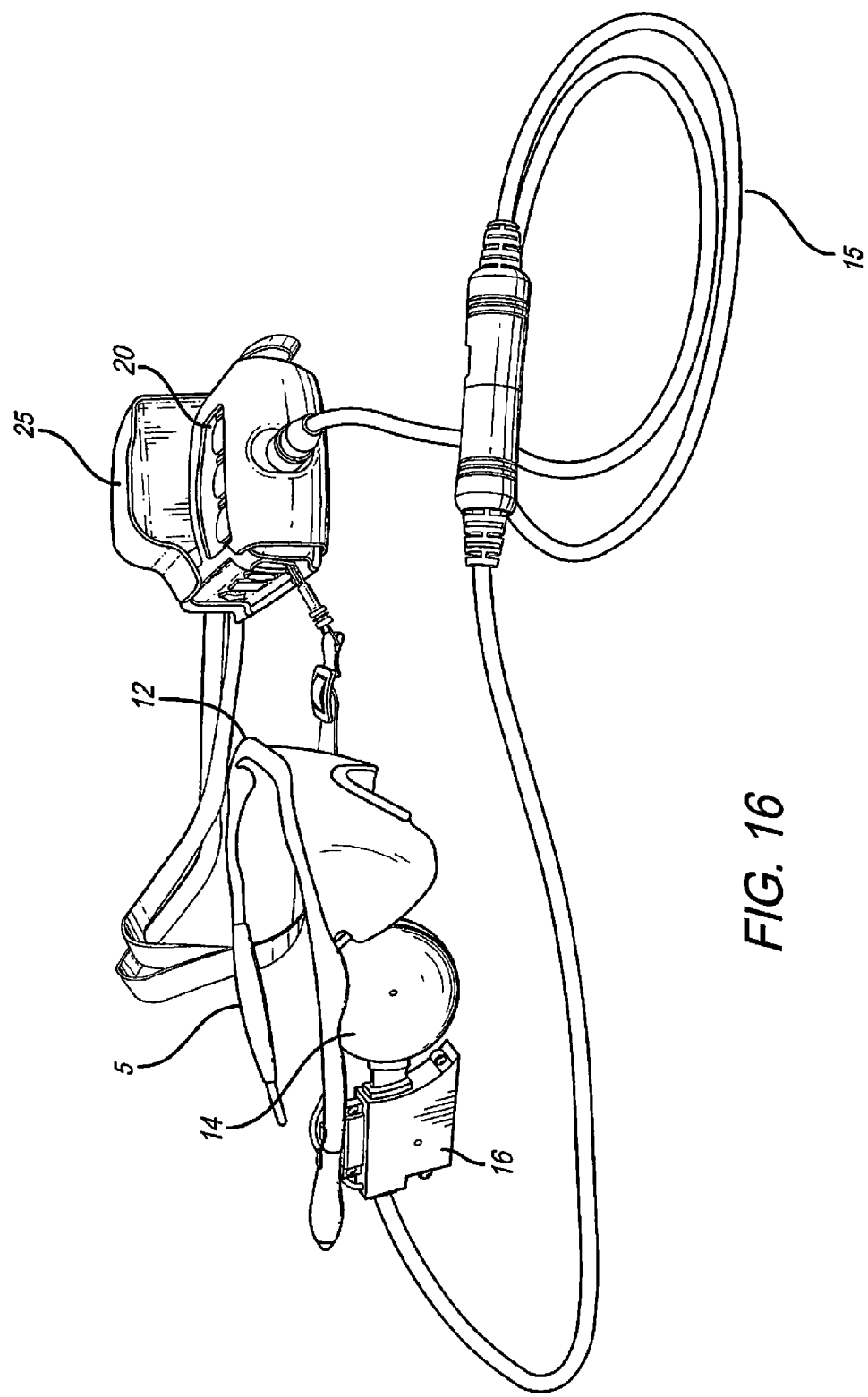
FIG. 16 shows the external portion of the visual prosthesis apparatus in a stand-alone mode, i.e. comprising the visor connected to a video processing unit.
Figure 17:
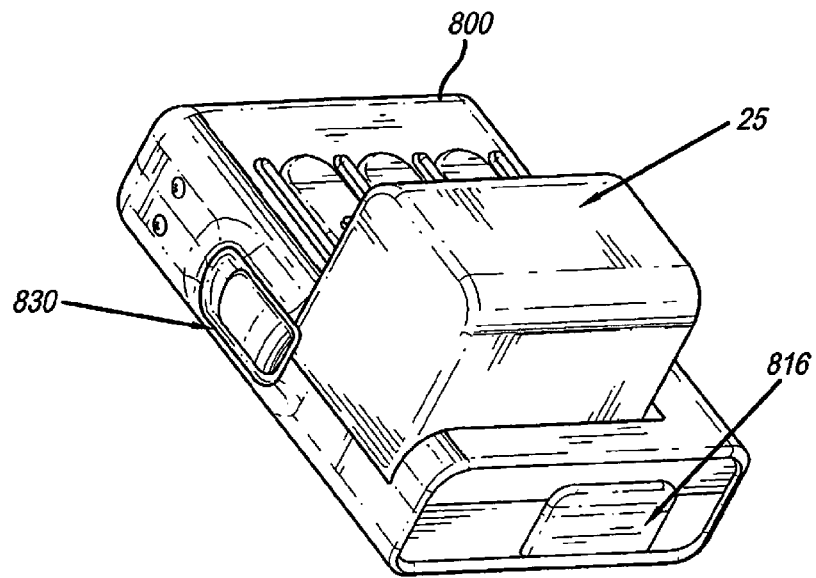
FIGS. 17-18 show the video processing unit in more detail already briefly shown with reference to FIGS. 15 and 16.

The visual prosthesis apparatus may operate in two modes: i) stand-alone mode and ii) communication mode Stand-Alone Mode Referring to FIG. 16, in the stand-alone mode, the video camera 12, on the glasses 5, captures a video image that is sent to the VPU 20. The VPU 20 processes the image from the camera 12 and transforms it into electrical stimulation patterns that are transmitted to the external coil 14. The external coil 14 sends the electrical stimulation patterns and power via radio-frequency (RF) telemetry to the implanted retinal stimulation system. The internal coil 116 of the retinal stimulation system 1 receives the RF commands from the external coil 14 and transmits them to the electronics package 4 that in turn delivers stimulation to the retina via the electrode array 2. Additionally, the retinal stimulation system 1 may communicate safety and operational status back to the VPU 20 by transmitting RF telemetry from the internal coil 116 to the external coil 14. The visual prosthesis apparatus may be configured to electrically activate the retinal stimulation system 1 only when it is powered by the VPU 20 through the external coil 14. The stand-alone mode may be used for clinical testing and/or at-home use by the subject.

Communication Mode

The communication mode may be used for diagnostic testing, psychophysical testing, patient fitting and downloading of stimulation settings to the VPU 20 before transmitting data from the VPU 20 to the retinal stimulation system 1 as is done for example in the stand-alone mode described above. Referring to FIG. 15, in the communication mode, the VPU 20 is connected to the Fitting System laptop 10 using cables 70, 45 and the optically isolated serial connection adapter 40. In this mode, laptop 10 generated stimuli may be presented to the subject and programming parameters may be adjusted and downloaded to the VPU 20. The Psychophysical Test System (PTS) laptop 30 connected to the Fitting System laptop 10 may also be utilized to perform more sophisticated testing and analysis as fully described in the related application U.S. application Ser. No. 11/796,425, filed on Apr. 27, 2007 which is incorporated herein by reference in its entirety.

In one embodiment, the functionality of the retinal stimulation system can also be tested pre-operatively and intra-operatively (i.e. before operation and during operation) by using an external coil 14, without the glasses 5, placed in close proximity to the retinal stimulation system 1. The coil 14 may communicate the status of the retinal stimulation system 1 to the VPU 20 that is connected to the Fitting System laptop 10 as shown in FIG. 15.

As discussed above, the VPU 20 processes the image from the camera 12 and transforms the image into electrical stimulation patterns for the retinal stimulation system. Filters such as edge detection filters may be applied to the electrical stimulation patterns for example by the VPU 20 to generate, for example, a stimulation pattern based on filtered video data that the VPU 20 turns into stimulation data for the retinal stimulation system. The images may then be reduced in resolution using a downscaling filter. In one exemplary embodiment, the resolution of the image may be reduced to match the number of electrodes in the electrode array 2010 of the retinal stimulation system. That is, if the electrode array has, for example, sixty electrodes, the image may be reduced to a sixty channel resolution. After the reduction in resolution, the image is mapped to stimulation intensity using for example a look-up table that has been derived from testing of individual subjects. Then, the VPU 20 transmits the stimulation parameters via forward telemetry to the retinal stimulation system in frames that may employ a cyclic redundancy check (CRC) error detection scheme.

Figure 18:
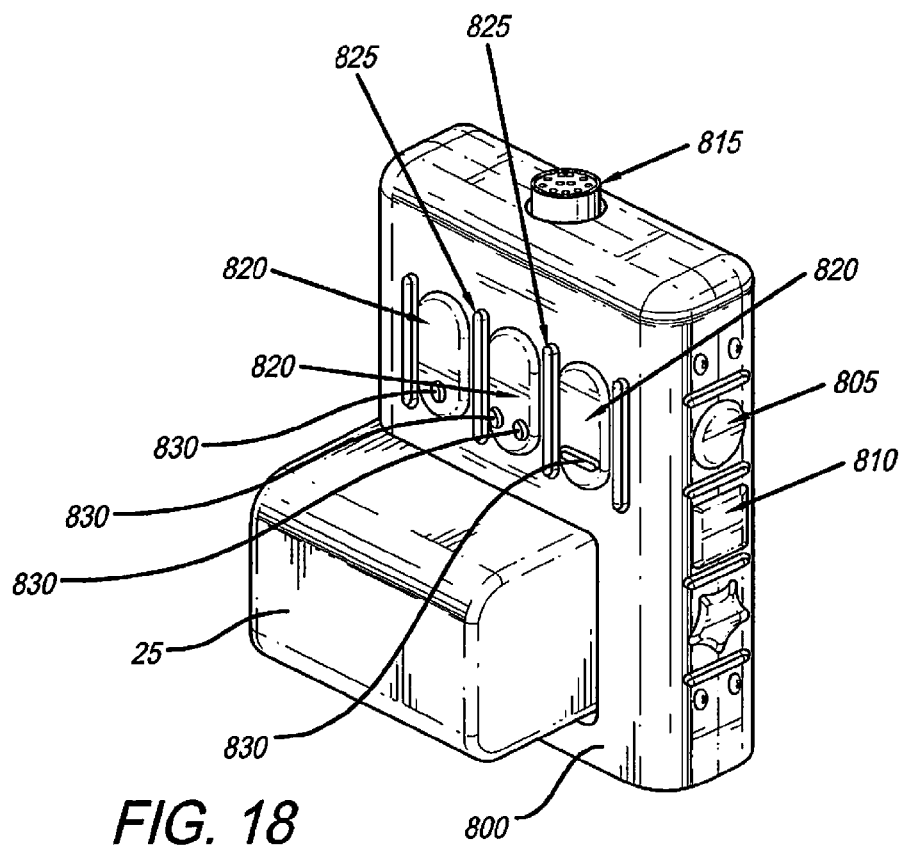

In one exemplary embodiment, the VPU 20 may be configured to allow the subject/patient i) to turn the visual prosthesis apparatus on and off, ii) to manually adjust settings, and iii) to provide power and data to the retinal stimulation system 1. Referring to FIGS. 15 and 16, the VPU 20 may comprise a case 800, power button 805 for turning the VPU 20 on and off, setting button 810, zoom buttons 820 for controlling the camera 12, connector port 815 for connecting to the Glasses 5, a connector port 816 for connecting to the laptop 10 through the connection adapter 40, indicator lights 825 to give visual indication of operating status of the system, the rechargeable battery 25 for powering the VPU 20, battery latch 830 for locking the battery 25 in the case 800, digital circuit boards (not shown), and a speaker (not shown) to provide audible alerts to indicate various operational conditions of the system. Because the VPU 20 is used and operated by a person with minimal or no vision, the buttons on the VPU 20 may be differently shaped and/or have special markings as shown in FIG. 18 to help the user identify the functionality of the button without having to look at it. As shown in FIG. 18, the power button 805 may be a circular shape while the settings button 820 may be square shape and the zoom buttons 820 may have special raised markings 830 to also identify each buttons functionality. One skilled in the art would appreciate that other shapes and markings can be used to identify the buttons without departing from the spirit and scope of the invention. For example, the markings can be recessed instead of raised.

In one embodiment, the indicator lights 825 may indicate that the VPU 20 is going through system start-up diagnostic testing when the one or more indicator lights 825 are blinking fast (more then once per second) and are green in color. The indicator lights 825 may indicate that the VPU 20 is operating normally when the one or more indicator lights 825 are blinking once per second and are green in color. The indicator lights 825 may indicate that the retinal stimulation system 1 has a problem that was detected by the VPU 20 at start-up diagnostic when the one or more indicator lights 825 are blinking for example once per five second and are green in color. The indicator lights 825 may indicate that the video signal from camera 12 is not being received by the VPU 20 when the one or more indicator lights 825 are always on and are amber color. The indicator lights 825 may indicate that there is a loss of communication between the retinal stimulation system 1 and the external coil 14 due to the movement or removal of Glasses 5 while the system is operational or if the VPU 20 detects a problem with the retinal stimulation system 1 and shuts off power to the retinal stimulation system 1 when the one or more indicator lights 825 are always on and are orange color. One skilled in the art would appreciate that other colors and blinking patterns can be used to give visual indication of operating status of the system without departing from the spirit and scope of the invention.

In one embodiment, a single short beep from the speaker (not shown) may be used to indicate that one of the buttons 825, 805 or 810 have been pressed. A single beep followed by two more beeps from the speaker (not shown) may be used to indicate that VPU 20 is turned off. Two beeps from the speaker (not shown) may be used to indicate that VPU 20 is starting up. Three beeps from the speaker (not shown) may be used to indicate that an error has occurred and the VPU 20 is about to shut down automatically. As would be clear to one skilled in the are different periodic beeping may also be used to indicate a low battery voltage warning, that there is a problem with the video signal, and/or there is a loss of communication between the retinal stimulation system 1 and the external coil 14. One skilled in the art would appreciate that other sounds can be used to give audio indication of operating status of the system without departing from the spirit and scope of the invention. For example, the beeps may be replaced by an actual prerecorded voice indicating operating status of the system.

In one exemplary embodiment, the VPU 20 is in constant communication with the retinal stimulation system through forward and backward telemetry. In this document, the forward telemetry refers to transmission from VPU 20 to the retinal stimulation system 1 and the backward telemetry refers to transmissions from the Retinal stimulation system 1 to the VPU 20. During the initial setup, the VPU 20 may transmit null frames (containing no stimulation information) until the VPU 20 synchronizes with the Retinal stimulation system 1 via the back telemetry. In one embodiment, an audio alarm may be used to indicate whenever the synchronization has been lost.

In order to supply power and data to the Retinal stimulation system 1, the VPU 20 may drive the external coil 14, for example, with a 3 MHz signal. To protect the subject, the retinal stimulation system 1 may comprise a failure detection circuit to detect direct current leakage and to notify the VPU 20 through back telemetry so that the visual prosthesis apparatus can be shut down.

The forward telemetry data (transmitted for example at 122.76 kHz) may be modulated onto the exemplary 3 MHz carrier using Amplitude Shift Keying (ASK), while the back telemetry data (transmitted for example at 3.8 kHz) may be modulated using Frequency Shift Keying (FSK) with, for example, 442 kHz and 457 kHz. The theoretical bit error rates can be calculated for both the ASK and FSK scheme assuming a ratio of signal to noise (SNR). The system disclosed in the present disclosure can be reasonably expected to see bit error rates of 10-5 on forward telemetry and 10-3 on back telemetry. These errors may be caught more than 99.998% of the time by both an ASIC hardware telemetry error detection algorithm and the VPU 20's firmware. For the forward telemetry, this is due to the fact that a 16-bit cyclic redundancy check (CRC) is calculated for every 1024 bits sent to the ASIC within electronics package 4 of the Retinal Stimulation System 1. The ASIC of the Retinal Stimulation System 1 verifies this CRC and handles corrupt data by entering a non-stimulating 'safe' state and reporting that a telemetry error was detected to the VPU 20 via back telemetry. During the 'safe' mode, the VPU 20 may attempt to return the implant to an operating state. This recovery may be on the order of milliseconds. The back telemetry words are checked for a 16-bit header and a single parity bit. For further protection against corrupt data being misread, the back telemetry is only checked for header and parity if it is recognized as properly encoded Bi-phase Mark Encoded (BPM) data. If the VPU 20 detects invalid back telemetry data, the VPU 20 immediately changes mode to a 'safe' mode where the Retinal Stimulation System 1 is reset and the VPU 20 only sends non-stimulating data frames. Back telemetry errors cannot cause the VPU 20 to do anything that would be unsafe.

Figure 19A:
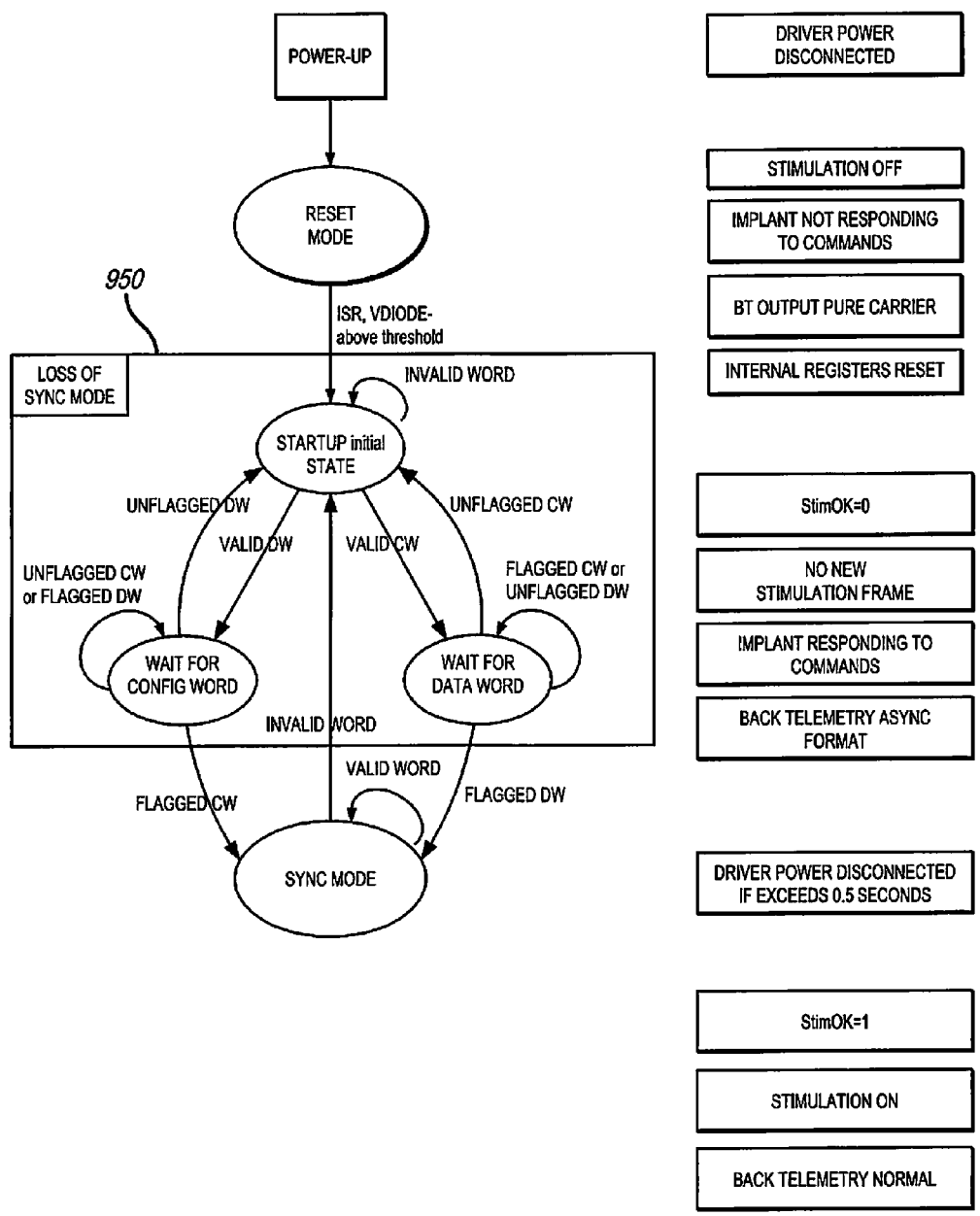
FIG. 19a shows a LOSS OF SYNC mode.

The response to errors detected in data transmitted by VPU 20 may begin at the ASIC of the Retinal Stimulation System 1. The Retinal Stimulation System 1 may be constantly checking the headers and CRCs of incoming data frames. If either the header or CRC check fails, the ASIC of the Retinal Stimulation System 1 may enter a mode called LOSS OF SYNC 950, shown in FIG. 19*a*. In LOSS OF SYNC mode 950, the Retinal Stimulation System 1 will no longer produce a stimulation output, even if commanded to do so by the VPU 20. This cessation of stimulation occurs after the end of the stimulation frame in which the LOSS OF SYNC mode 950 is entered, thus avoiding the possibility of unbalanced pulses not completing stimulation. If the Retinal Stimulation System 1 remains in a LOSS OF SYNC mode 950 for 1 second or more (for example, caused by successive errors in data transmitted by VPU 20), the ASIC of the Retinal Stimulation System 1 disconnects the power lines to the stimulation pulse drivers. This eliminates the possibility of any leakage from the power supply in a prolonged LOSS OF SYNC mode 950. From the LOSS OF SYNC mode 950, the Retinal Stimulation System 1 will not re-enter a stimulating mode until it has been properly initialized with valid data transmitted by the VPU 20.

In addition, the VPU 20 may also take action when notified of the LOSS OF SYNC mode 950. As soon as the Retinal Stimulation System 1 enters the LOSS OF SYNC mode 950, the Retinal Stimulation System 1 reports this fact to the VPU 20 through back telemetry. When the VPU 20 detects that the Retinal Stimulation System 1 is in LOSS OF SYNC mode 950, the VPU 20 may start to send 'safe' data frames to the Retinal Stimulation System 1. 'Safe' data is data in which no stimulation output is programmed and the power to the stimulation drivers is also programmed to be off. The VPU 20 will not send data frames to the Retinal Stimulation System 1 with stimulation commands until the VPU 20 first receives back telemetry from the Retinal Stimulation System 1 indicating that the Retinal Stimulation System 1 has exited the LOSS OF SYNC mode 950. After several unsuccessful retries by the VPU 20 to take the implant out of LOSS OF SYNC mode 950, the VPU 20 will enter a Low Power Mode (described below) in which the implant is only powered for a very short time. In this time, the VPU 20 checks the status of the implant. If the implant continues to report a LOSS OF SYNC mode 950, the VPU 20 turns power off to the Retinal Stimulation System 1 and tries again later. Since there is no possibility of the implant electronics causing damage when it is not powered, this mode is considered very safe.

Due to an unwanted electromagnetic interference (EMI) or electrostatic discharge (ESD) event the VPU 20 data, specifically the VPU firmware code, in RAM can potentially get corrupted and may cause the VPU 20 firmware to freeze. As a result, the VPU 20 firmware will stop resetting the hardware watchdog circuit, which may cause the system to reset. This will cause the watchdog timer to expire causing a system reset in, for example, less than 2.25 seconds. Upon recovering from the reset, the VPU 20 firmware logs the event and shuts itself down. VPU 20 will not allow system usage after this occurs once. This prevents the VPU 20 code from freezing for extended periods of time and hence reduces the probability of the VPU sending invalid data frames to the implant.

Supplying power to the Retinal stimulation system 1 can be a significant portion of the VPU 20's total power consumption. When the Retinal stimulation system 1 is not within receiving range to receive either power or data from the VPU 20, the power used by the VPU 20 is wasted.

Power delivered to the Retinal stimulation system 1 may be dependant on the orientation of the coils 14 and 116. The power delivered to the Retinal stimulation system 1 may be controlled, for example, via the VPU 20 every 16.6 ms. The Retinal stimulation system 1 may report how much power it receives and the VPU 20 may adjust the power supply voltage of the RF driver to maintain a required power level on the Retinal stimulation system 1. Two types of power loss may occur: 1) long term (>~1 second) and 2) short term (<~1 second). The long term power loss may be caused, for example, by a subject removing the Glasses 5.

Figure 19B:
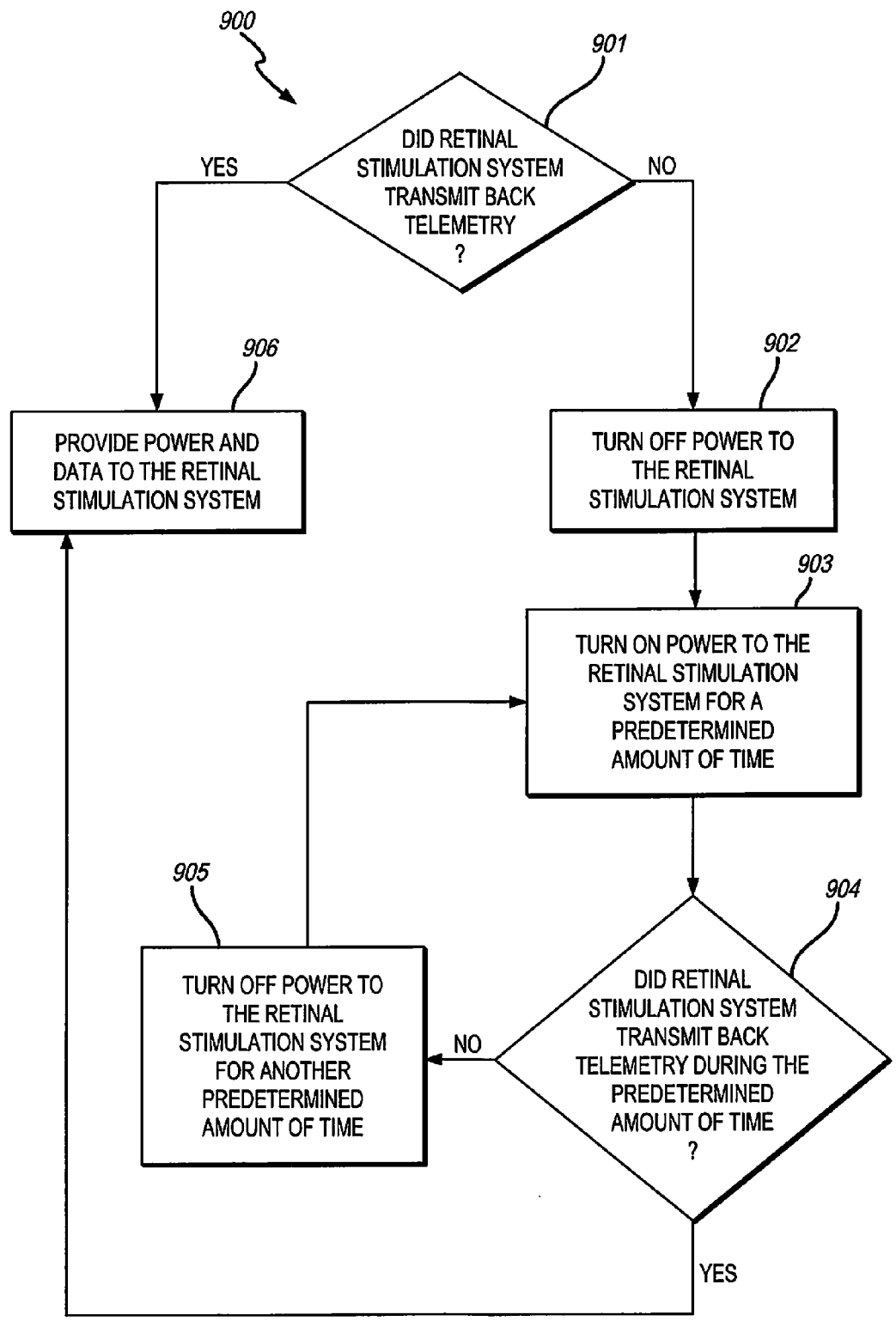
FIG. 19b shows an exemplary block diagram of the steps taken when VPU does not receive back telemetry from the Retinal stimulation system.

In one exemplary embodiment, the Low Power Mode may be implemented to save power for VPU 20. The Low Power Mode may be entered, for example, anytime the VPU 20 does not receive back telemetry from the Retinal stimulation system 1. Upon entry to the Low Power Mode, the VPU 20 turns off power to the Retinal stimulation system 1. After that, and periodically, the VPU 20 turns power back on to the Retinal stimulation system 1 for an amount of time just long enough for the presence of the Retinal stimulation system 1 to be recognized via its back telemetry. If the Retinal stimulation system 1 is not immediately recognized, the controller again shuts off power to the Retinal stimulation system 1. In this way, the controller 'polls' for the passive Retinal stimulation system 1 and a significant reduction in power used is seen when the Retinal stimulation system 1 is too far away from its controller device. FIG. 19b depicts an exemplary block diagram 900 of the steps taken when the VPU 20 does not receive back telemetry from the Retinal stimulation system 1. If the VPU 20 receives back telemetry from the Retinal stimulation system 1 (output "YES" of step 901), the Retinal stimulation system 1 may be provided with power and data (step 906). If the VPU 20 does not receive back telemetry from the Retinal stimulation system 1 (output "NO" of step 901), the power to the Retinal stimulation system 1 may be turned off. After some amount of time, power to the Retinal stimulation system 1 may be turned on again for enough time to determine if the Retinal stimulation system 1 is again transmitting back telemetry (step 903). If the Retinal stimulation system 1 is again transmitting back telemetry (step 904), the Retinal stimulation system 1 is provided with power and data (step 906). If the Retinal stimulation system 1 is not transmitting back telemetry (step 904), the power to the Retinal stimulation system 1 may again be turned off for a predetermined amount of time (step 905) and the process may be repeated until the Retinal stimulation system 1 is again transmitting back telemetry.

Figure 19C:
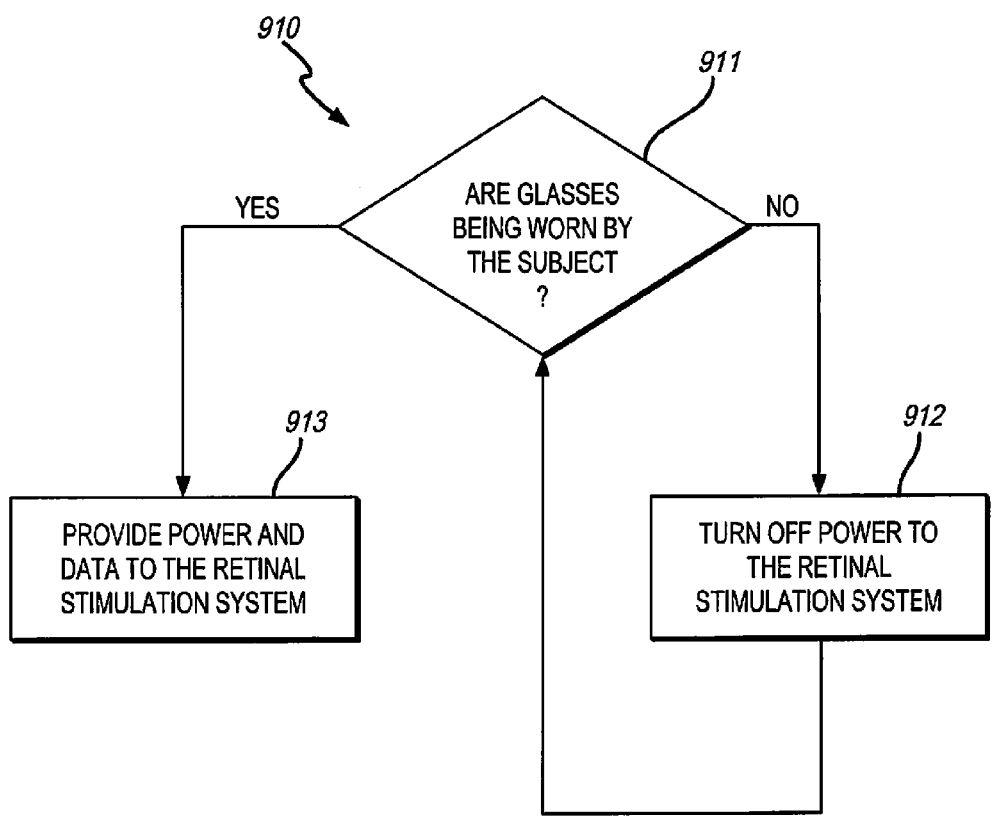
FIG. 19c shows an exemplary block diagram of the steps taken when the subject is not wearing Glasses.

In another exemplary embodiment, the Low Power Mode may be entered whenever the subject is not wearing the Glasses 5. In one example, the Glasses 5 may contain a capacitive touch sensor (not shown) to provide the VPU 20 digital information regarding whether or not the Glasses 5 are being worn by the subject. In this example, the Low Power Mode may be entered whenever the capacitive touch sensor detects that the subject is not wearing the Glasses 5. That is, if the subject removes the Glasses 5, the VPU 20 will shut off power to the external coil 14. As soon as the Glasses 5 are put back on, the VPU 20 will resume powering the external coil 14. FIG. 19c depicts an exemplary block diagram 910 of the steps taken when the capacitive touch sensor detects that the subject is not wearing the Glasses 5. If the subject is wearing Glasses 5 (step 911), the Retinal stimulation system 1 is provided with power and data (step 913). If the subject is not wearing Glasses 5 (step 911), the power to the Retinal stimulation system 1 is turned off (step 912) and the process is repeated until the subject is wearing Glasses 5.

Figures 1, 20:
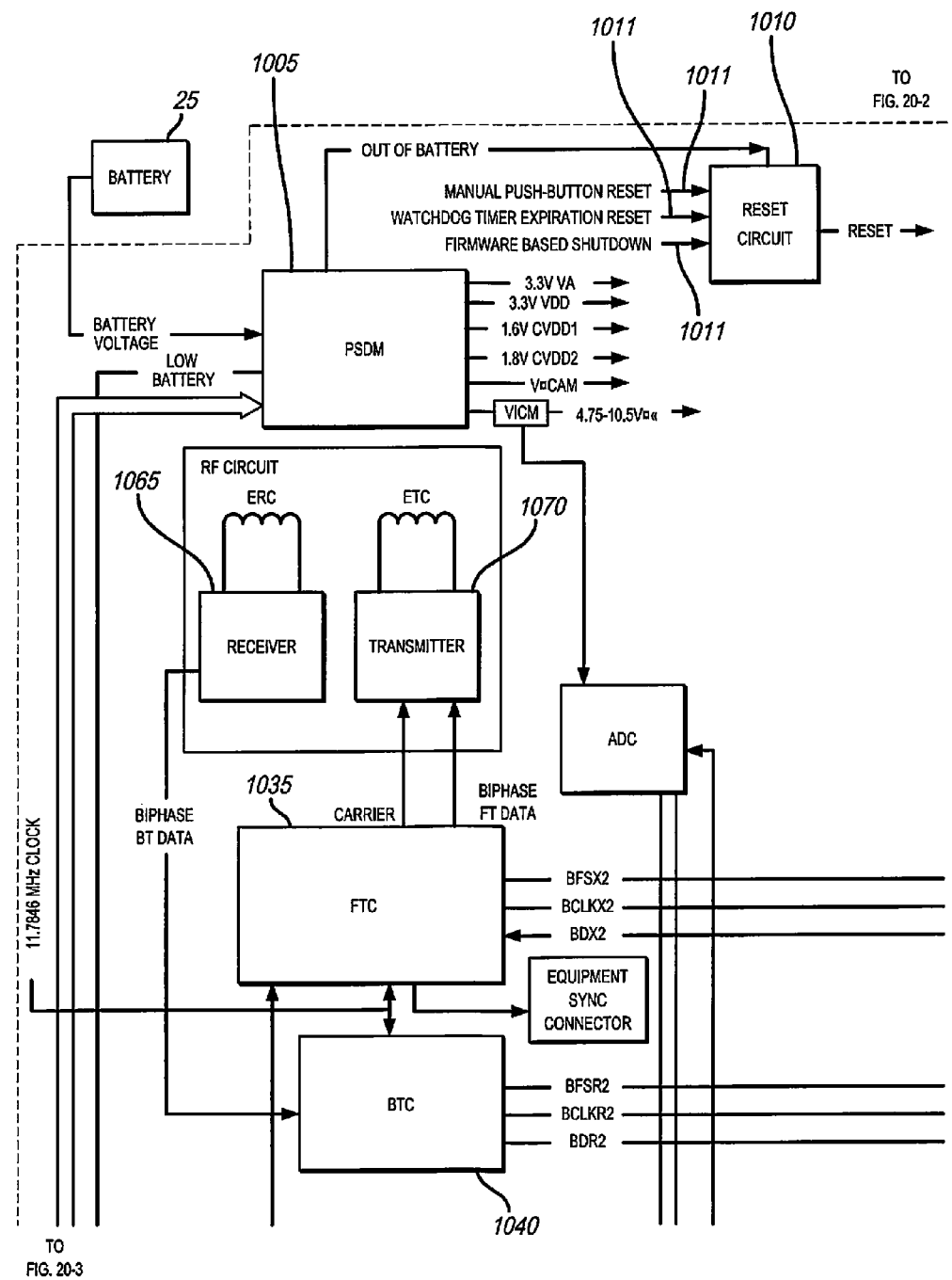
Figures 2, 20:
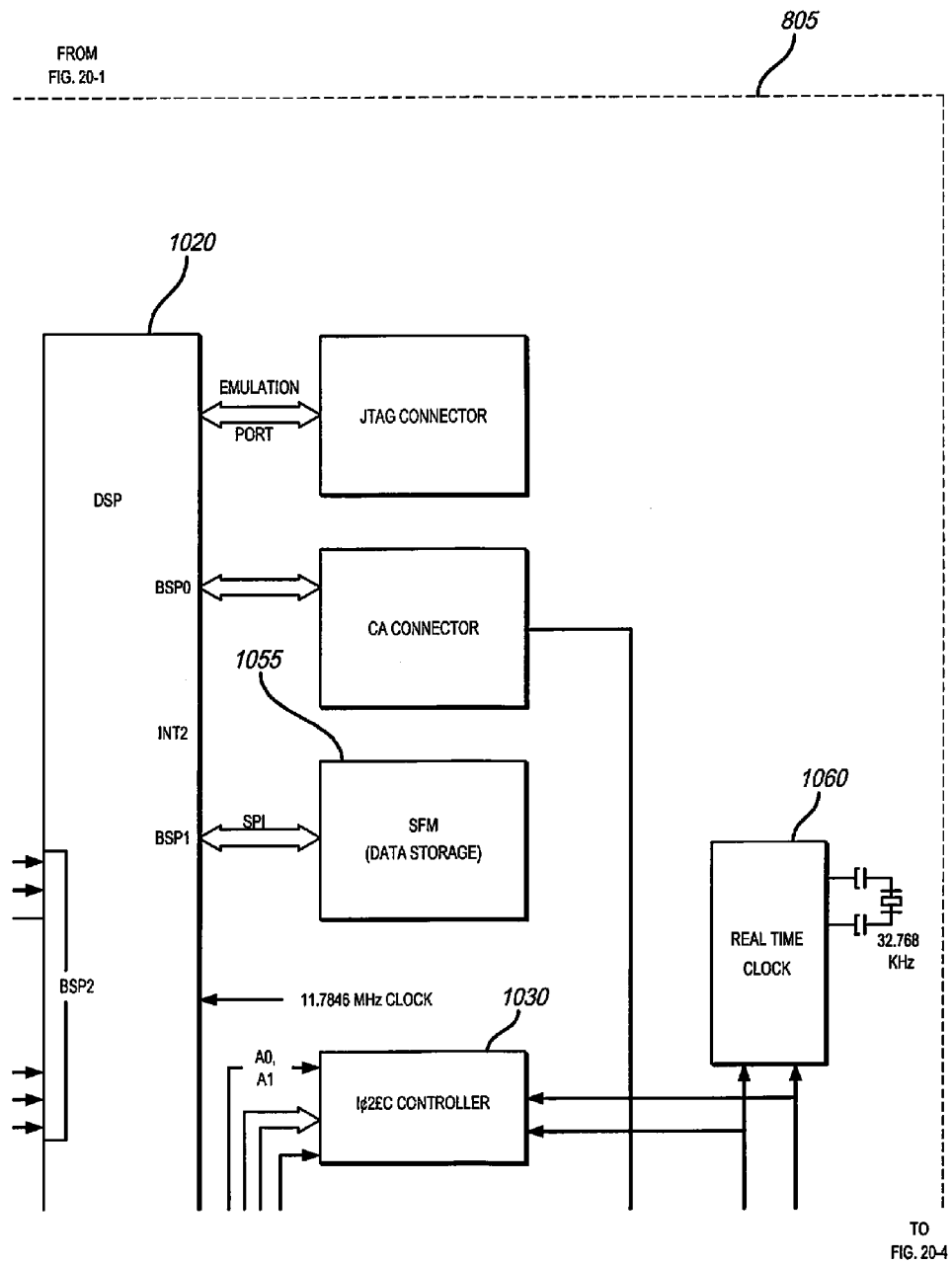
Figures 3, 20:
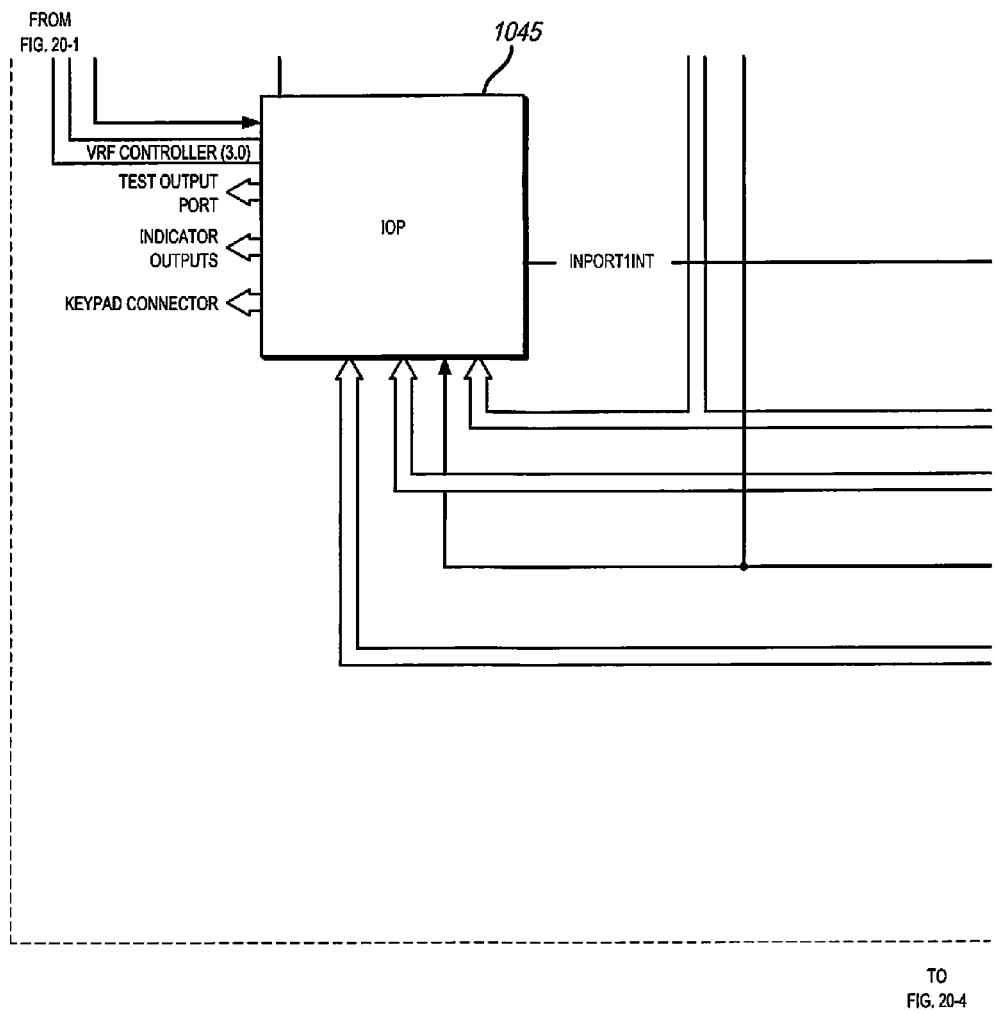
Figures 4, 20:
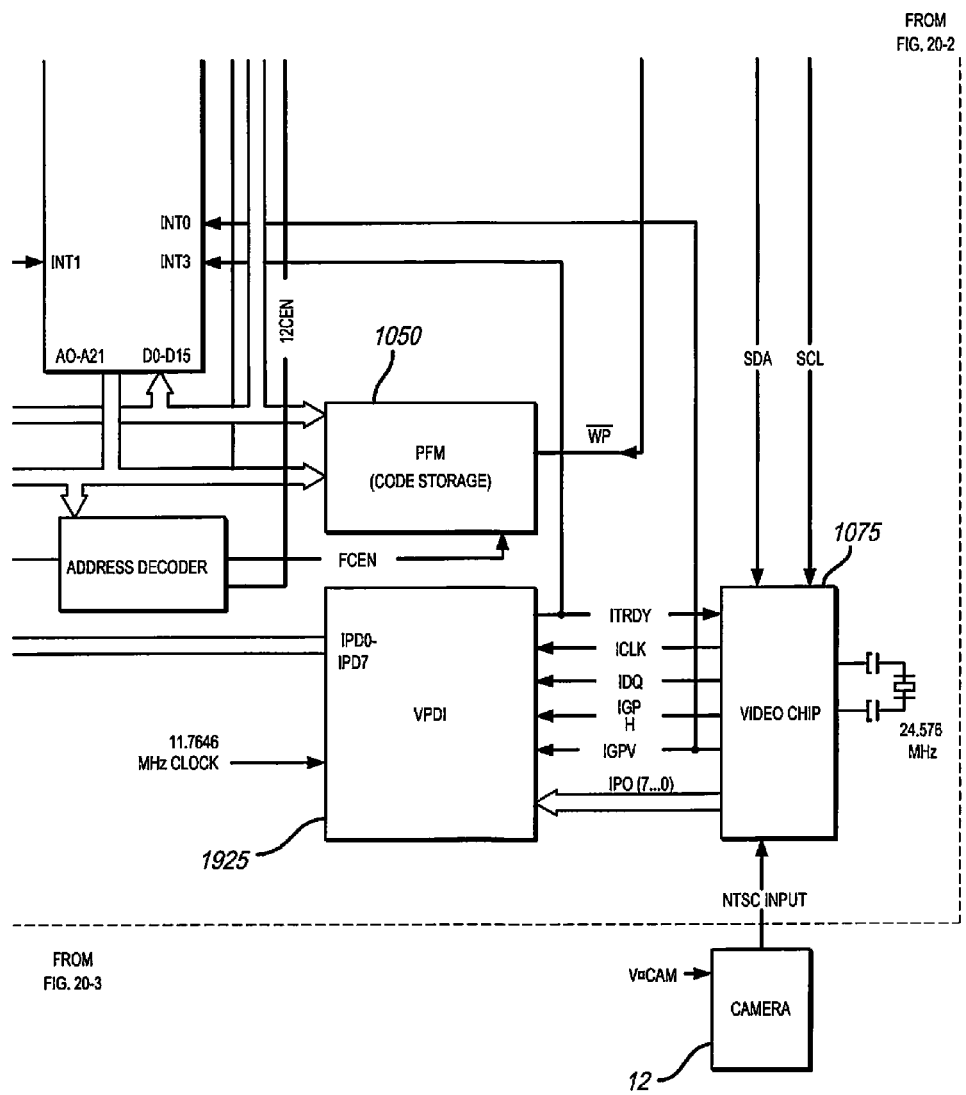

One exemplary embodiment of the VPU 20 is shown in FIG. 20. The VPU 20 may comprise: a Power Supply, a Distribution and Monitoring Circuit (PSDM) 1005, a Reset Circuit 1010, a System Main Clock (SMC) source (not shown), a Video Preprocessor Clock (VPC) source (not shown), a Digital Signal Processor (DSP) 1020, Video Preprocessor Data Interface 1025, a Video Preprocessor 1075, an I²C Protocol Controller 1030, a Complex Programmable Logic device (CPLD) (not shown), a Forward Telemetry Controller (FTC) 1035, a Back Telemetry Controller (BTC) 1040, Input/Output Ports 1045, Memory Devices like a Parallel Flash Memory (PFM) 1050 and a Serial Flash Memory (SFM) 1055, a Real Time Clock 1060, an RF Voltage and Current Monitoring Circuit (VIMC) (not shown), a speaker and/or a buzzer, an RF receiver 1065, and an RF transmitter 1070.

The Power Supply, Distribution and Monitoring Circuit (PSDM) 1005 may regulate a variable battery voltage to several stable voltages that apply to components of the VPU 20. The Power Supply, Distribution and Monitoring Circuit (PSDM) 1005 may also provide low battery monitoring and depleted battery system cutoff. The Reset Circuit 1010 may have reset inputs 1011 that are able to invoke system level rest. For example, the reset inputs 1011 may be from a manual push-button reset, a watchdog timer expiration, and/or firmware based shutdown. The System Main Clock (SMC) source is a clock source for DSP 1020 and CPLD. The Video Preprocessor Clock (VPC) source is a clock source for the Video Processor. The DSP 1020 may act as the central processing unit of the VPU 20. The DSP 1020 may communicate with the rest of the components of the VPU 20 through parallel and serial interfaces. The Video Processor 1075 may convert the NTSC signal from the camera 12 into a down-scaled resolution digital image format. The Video Processor 1075 may comprise a video decoder (not shown) for converting the NTSC signal into high-resolution digitized image and a video scaler (not shown) for scaling down the high-resolution digitized image from the video decoder to an intermediate digitized image resolution. The video decoder may be composed of an Analog Input Processing, Chrominance and Luminance Processing and Brightness Contrast and Saturation (BSC) Control circuits. The video scaler may be composed of Acquisition control, Pre-scaler, BSC-control, Line Buffer and Output Interface. The I²C Protocol Controller 1030 may serve as a link between the DSP 1020 and the I²C bus. The I²C Protocol Controller 1030 may be able to convert the parallel bus interface of the DSP 1020 to the I²C protocol bus or vise versa. The I²C Protocol Controller 1030 may also be connected to the Video Processor 1075 and the Real Time Clock 1060. The VPDI 1025 may contain a tri-state machine to shift video data from Video Preprocessor 1075 to the DSP 1020. The Forward Telemetry Controller (FTC) 1035 packs 1024 bits of forward telemetry data into a forward telemetry frame. The FTC 1035 retrieves the forward telemetry data from the DSP 1020 and converts the data from logic level to biphase marked data. The Back Telemetry Controller (BTC) 1040 retrieves the biphase marked data from the RF receiver 1065, decodes it, and generates the BFSR and BCLKR for the DSP 1020. The Input/Output Ports 1045 provide expanded IO functions to access the CPLD on-chip and off-chip devices. The Parallel Flash Memory (PFM) 1050 may be used to store executable code and the Serial Flash Memory (SFM) 1055 may provide Serial Port Interface (SPI) for data storage. The VIMC may be used to sample and monitor RF transmitter 1070 current and voltage in order to monitor the integrity status of the retinal stimulation system 1.

FIG. 22 shows a perspective view of the implanted portion of the preferred visual prosthesis. A flexible circuit 2001 includes a flexible circuit electrode array 2010 which is mounted by a retinal tack (not shown) or similar means to the epiretinal surface. The flexible circuit electrode array 2010 is electrically coupled by a flexible circuit cable 2012, which pierces the sclera and is electrically coupled to an electronics package 2014, external to the sclera.

The electronics package 2014 is electrically coupled to a secondary inductive coil 2016. Preferably the secondary inductive coil 2016 is made from wound wire. Alternatively, the secondary inductive coil 2016 may be made from a flexible circuit polymer sandwich with wire traces deposited between layers of flexible circuit polymer. The secondary inductive coil receives power and data from a primary inductive coil 2017, which is external to the body. The electronics package 2014 and secondary inductive coil 2016 are held together by the molded body 2018. The molded body 18 holds the electronics package 2014 and secondary inductive coil 16 end to end. The secondary inductive coil 16 is placed around the electronics package 2014 in the molded body 2018. The molded body 2018 holds the secondary inductive coil 2016 and electronics package 2014 in the end to end orientation and minimizes the thickness or height above the sclera of the entire device. The molded body 2018 may also include suture tabs 2020. The molded body 2018 narrows to form a strap 2022 which surrounds the sclera and holds the molded body 2018, secondary inductive coil 2016, and electronics package 2014 in place. The molded body 2018, suture tabs 2020 and strap 2022 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 2016 and molded body 2018 are preferably oval shaped. A strap 2022 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

Figure 23:
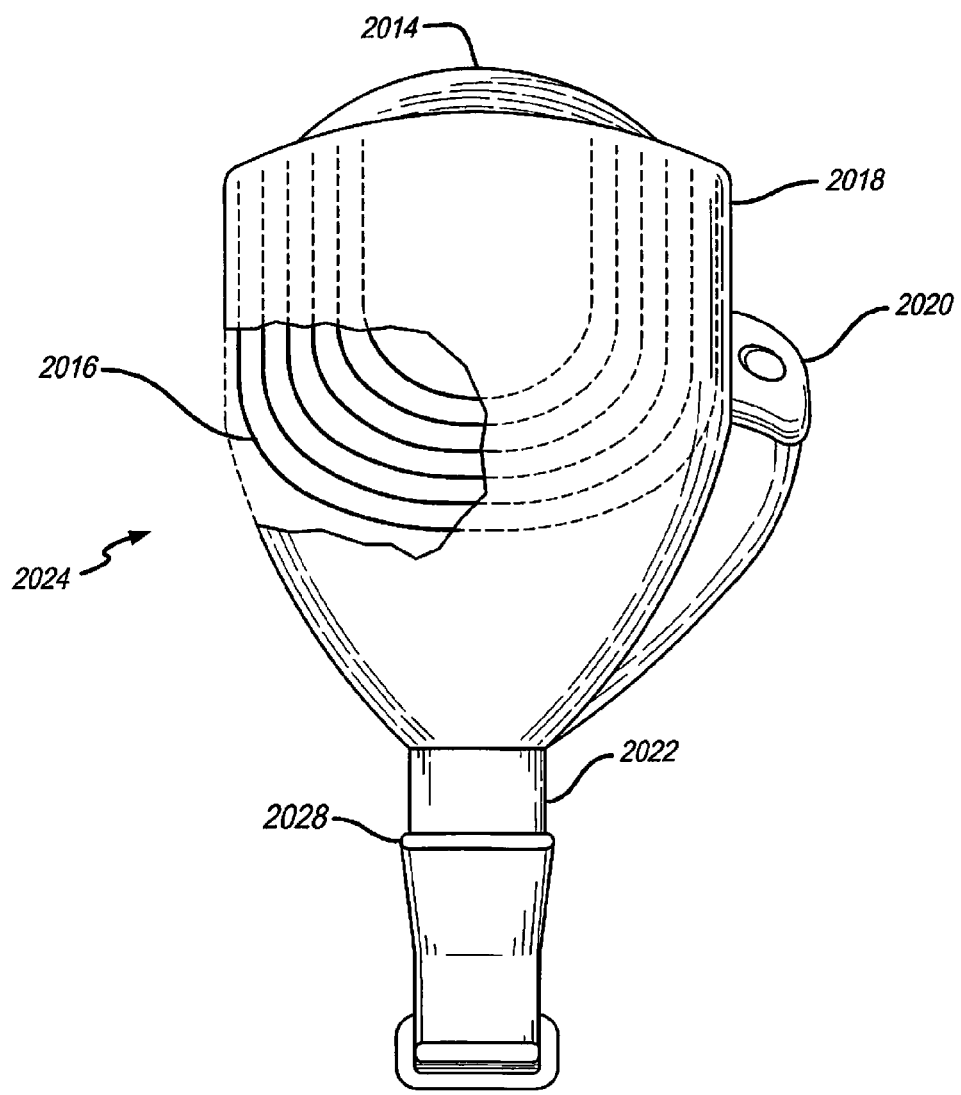
FIG. 23 is a side view of the implanted portion of the preferred visual prosthesis showing the fan tail in more detail.

FIG. 23 shows a side view of the implanted portion of the visual prosthesis, in particular, emphasizing the fan tail 2024. When implanting the visual prosthesis, it is necessary to pass the strap 2022 under the eye muscles to surround the sclera. The secondary inductive coil 2016 and molded body 2018 must also follow the strap 2022 under the lateral rectus muscle on the side of the sclera. The implanted portion of the visual prosthesis is very delicate. It is easy to tear the molded body 2018 or break wires in the secondary inductive coil 2016. In order to allow the molded body 18 to slide smoothly under the lateral rectus muscle, the molded body 2018 is shaped in the form of a fan tail 2024 on the end opposite the electronics package 2014. The strap 2022 further includes a hook 2028 the aids the surgeon in passing the strap under the rectus muscles.

Figure 24:
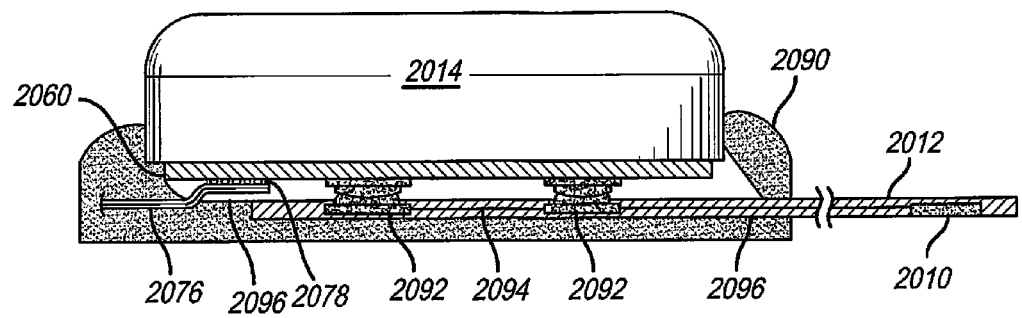
FIG. 24 is a view of the completed package attached to an electrode array.

Referring to FIG. 24, the flexible circuit 1, includes platinum conductors 2094 insulated from each other and the external environment by a biocompatible dielectric polymer 2096, preferably polyimide. One end of the array contains exposed electrode sites that are placed in close proximity to the retinal surface 2010. The other end contains bond pads 2092 that permit electrical connection to the electronics package 2014. The electronic package 2014 is attached to the flexible circuit 1 using a flip-chip bumping process, and epoxy underfilled. In the flip-chip bumping process, bumps containing conductive adhesive placed on bond pads 2092 and bumps containing conductive adhesive placed on the electronic package 2014 are aligned and melted to build a conductive connection between the bond pads 2092 and the electronic package 2014. Leads 2076 for the secondary inductive coil 2016 are attached to gold pads 2078 on the ceramic substrate 2060 using thermal compression bonding, and are then covered in epoxy. The electrode array cable 2012 is laser welded to the assembly junction and underfilled with epoxy. The junction of the secondary inductive coil 2016, array 2001, and electronic package 2014 are encapsulated with a silicone overmold 2090 that connects them together mechanically. When assembled, the hermetic electronics package 2014 sits about 3 mm away from the end of the secondary inductive coil.

Since the implant device is implanted just under the conjunctiva it is possible to irritate or even erode through the conjunctiva. Eroding through the conjunctiva leaves the body open to infection. We can do several things to lessen the likelihood of conjunctiva irritation or erosion. First, it is important to keep the over all thickness of the implant to a minimum. Even though it is advantageous to mount both the electronics package 2014 and the secondary inductive coil 2016 on the lateral side of the sclera, the electronics package 2014 is mounted higher than, but not covering, the secondary inductive coil 2016. In other words the thickness of the secondary inductive coil 2016 and electronics package should not be cumulative.

It is also advantageous to place protective material between the implant device and the conjunctiva. This is particularly important at the scleratomy, where the thin film electrode array cable 2012 penetrates the sclera. The thin film electrode array cable 2012 must penetrate the sclera through the pars plana, not the retina. The scleratomy is, therefore, the point where the device comes closest to the conjunctiva. The protective material can be provided as a flap attached to the implant device or a separate piece placed by the surgeon at the time of implantation. Further material over the scleratomy will promote healing and sealing of the scleratomy. Suitable materials include DACRON®, TEFLON®, GORETEX® (ePTFE), TUTOPLAST® (sterilized sclera), MERSILENE® (polyester) or silicone.

Figure 25:
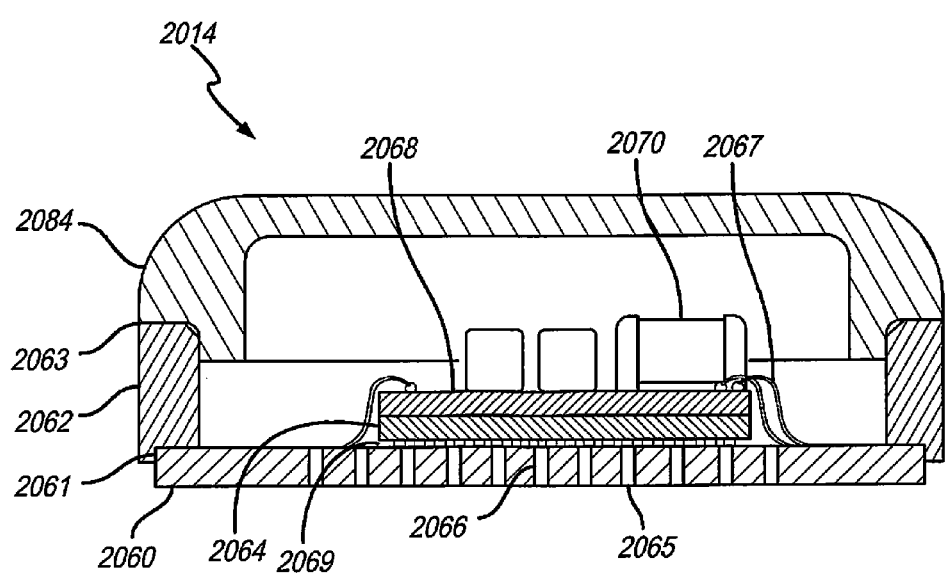
FIG. 25 is a cross-section of the package.

Referring to FIG. 25, the package 2014 contains a ceramic substrate 2060, with metalized vias 2065 and thin-film metallization 2066. The package 2014 contains a metal case wall 2062 which is connected to the ceramic substrate 2060 by braze joint 2061. On the ceramic substrate 2060 an underfill 2069 is applied. On the underfill 69 an integrated circuit chip 2064 is positioned. On the integrated circuit chip 2064 a ceramic hybrid substrate 2068 is positioned. On the ceramic hybrid substrate 2068 passives 2070 are placed. Wirebonds 2067 are leading from the ceramic substrate 2060 to the ceramic hybrid substrate 2068. A metal lid 2084 is connected to the metal case wall 2062 by laser welded joint 2063 whereby the package 2014 is sealed.

Accordingly, what has been shown is an improved visual prosthesis and an improved method for limiting power consumption in a visual prosthesis. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. A method fitting a visual prosthesis comprising:
providing a touch screen monitor connected to a computer:
projecting an image on the touch screen monitor in an actual location;
asking a subject to indicate the perceived location of the image by touching the touch screen monitor;
providing feed back to subject as the accuracy of the perceived location;
calculating a difference between the actual location and the perceived location in the computer; and
adjusting the visual prosthesis based on the difference.
2. The method according to claim 1, further comprising:
repeating the steps of claim 1, at different times;

storing the difference in the computer for each of the different times; and refining the adjustment of the visual prosthesis by stored difference values.

3. The method according to claim 1, further comprising:

recording a camera sampling position of the visual prosthesis camera; and refining the adjustment of the visual prosthesis by the camera sampling position.

4. The method according to claim 1, wherein the feedback is auditory feedback.

5. The method according to claim 4, wherein the auditory feedback is an indication of right or wrong.

6. The method according to claim 4, wherein the auditory feedback is an indication of the direction and distance of the error.

7. The method according to claim 1, further comprising:

calculating a confidence interval based on error rates; and excluding data with a confidence interval less that a predetermined minimum.

8. The method according to claim 7, wherein the predetermined minimum is 95%.

9. The method according to claim 7, wherein the confidence interval is calculated by t-distributions.

10. The method according to claim 7, further comprising calculating separate confidence intervals for vertical and horizontal errors and excluding data with vertical confidence interval of less than a predetermined amount, and excluding data with a horizontal confidence interval of less than a predetermined amount.

11. The method according to claim 10, wherein the predetermined amount is 95%.

\* \* \* \* \*